United States Patent
Imamura

(10) Patent No.: US 12,414,718 B2
(45) Date of Patent: Sep. 16, 2025

(54) EARPHONE, INFORMATION PROCESSING DEVICE, AND INFORMATION PROCESSING METHOD

(71) Applicant: VIE, Inc., Kanagawa (JP)

(72) Inventor: Yasuhiko Imamura, Kanagawa (JP)

(73) Assignee: VIE, Inc., Kanagawa (JP)

( * ) Notice: Subject to any disclaimer, the term of this patent is extended or adjusted under 35 U.S.C. 154(b) by 777 days.

(21) Appl. No.: 17/767,359

(22) PCT Filed: Jul. 31, 2020

(86) PCT No.: PCT/JP2020/029385
§ 371 (c)(1),
(2) Date: Apr. 7, 2022

(87) PCT Pub. No.: WO2021/070456
PCT Pub. Date: Apr. 15, 2021

(65) Prior Publication Data
US 2022/0386919 A1 Dec. 8, 2022

(30) Foreign Application Priority Data
Oct. 8, 2019 (JP) .................. 2019-185473

(51) Int. Cl.
*A61B 5/25* (2021.01)
*A61B 5/00* (2006.01)
(Continued)

(52) U.S. Cl.
CPC .............. *A61B 5/25* (2021.01); *A61B 5/372* (2021.01); *H04R 1/105* (2013.01)

(58) Field of Classification Search
None
See application file for complete search history.

(56) References Cited

U.S. PATENT DOCUMENTS 3,671,685 A * 6/1972 McCabe .............. H04R 1/1016
381/338
2009/0041284 A1 2/2009 Tanaka et al.
(Continued)

FOREIGN PATENT DOCUMENTS

| CN | 204072066 U | | 1/2015 |
| JP | H10243492 A | * | 9/1998 |

(Continued)

OTHER PUBLICATIONS

International Search Report mailed Oct. 27, 2020 for International Application No. PCT/JP2020/029385, with translation, 6 pages.

*Primary Examiner* — Linda C Dvorak
*Assistant Examiner* — Nicholas S Borsch
(74) *Attorney, Agent, or Firm* — SQUIRE PATTON BOGGS (US) LLP

(57) ABSTRACT

Provided is an earphone in which electroencephalogram electrodes come into close contact more readily when worn. An earphone includes a housing having elasticity on at least one end portion side outer layer, a speaker accommodated inside the housing, and an eartip that is fixed on the end portion side of the housing having the elasticity, and that includes a sound conduit portion through which sound from the speaker passes, and an elastic electrode that performs sensing of an electroencephalogram of a wearer.

4 Claims, 27 Drawing Sheets

(51) Int. Cl.
*A61B 5/372* (2021.01)
*H04R 1/10* (2006.01)

(56) References Cited

U.S. PATENT DOCUMENTS

| | | | |
|---|---|---|---|
| 2009/0202096 A1* | 8/2009 | Ryann | H04R 1/1016 |
| | | | 381/374 |
| 2010/0217100 A1* | 8/2010 | LeBoeuf | A61B 5/6826 |
| | | | 600/382 |
| 2012/0172744 A1 | 7/2012 | Kato et al. | |
| 2013/0005303 A1* | 1/2013 | Song | A61B 5/02438 |
| | | | 455/411 |
| 2014/0303459 A1* | 10/2014 | Wada | A61B 5/1135 |
| | | | 600/301 |
| 2018/0275950 A1 | 9/2018 | Takagi et al. | |
| 2020/0359907 A1 | 11/2020 | Kashiwase | |

FOREIGN PATENT DOCUMENTS

| | | |
|---|---|---|
| JP | 2008-161429 A | 7/2008 |
| JP | 2009-044429 A | 2/2009 |
| JP | 2011-023974 A | 2/2011 |
| JP | 2012-074805 A | 4/2012 |
| JP | 2014-147023 A | 8/2014 |
| JP | 3209356 U | 3/2017 |
| JP | 2018-078398 A | 5/2018 |
| JP | 2018-159908 A | 10/2018 |
| JP | 2019-024758 A | 2/2019 |
| JP | 2019-037547 A | 3/2019 |
| JP | 2019-146275 A | 8/2019 |
| WO | WO 2011/135789 A1 | 11/2011 |

* cited by examiner

EARPHONE, INFORMATION PROCESSING DEVICE, AND INFORMATION PROCESSING METHOD

CROSS-REFERENCE TO RELATED APPLICATIONS

The present application is a national-stage filing under 37 USC 371 (c) of International Application No. PCT/JP2020/029385, filed Jul. 31, 2020, which claims the benefit and priority of Japanese Patent Application No. JP 2019-185473, filed on Oct. 8, 2019, the entire contents of each of which are herein incorporated by reference in their entirety for all purposes.

TECHNICAL FIELD

The present invention relates to an earphone, an information processing device, and an information processing method.

BACKGROUND ART

There conventionally are known earphones that acquire electroencephalogram signals (e.g., see Patent Document 1).

CITATION LIST

Patent Document

Patent Document 1: Patent Publication JP-A-2018-159908

SUMMARY

Technical Problem

When acquiring electroencephalogram signals, placing electrodes for electroencephalography in close contact with the user is important in order to acquire electroencephalogram signals with good precision. However, positions of electrodes are not decided in accordance with the shapes of ears and ear canals that differ from one user to another in conventional earphones, and accordingly electrodes for electroencephalography were not necessarily in close contact with sensing positions for users having various shapes of ears and ear canals. Also, when evaluating states from electroencephalogram signals, evaluation is normally performed using a generalized model in which electroencephalogram signals and states of a large indefinite number of users have been learned in advance, and states are not necessarily being appropriately estimated in accordance with electroencephalogram signals that differ from one user to another.

Accordingly, it is an object of one aspect of the present invention to provide an earphone in which electroencephalogram electrodes come into close contact more readily when worn. Also, it is an object of another aspect of the present invention to appropriately estimate the state of a wearer from electroencephalogram signals using a model generated customized for the wearer.

Solution to Problem

An earphone according to one aspect of the present invention includes a housing having elasticity on at least one end portion side outer layer, a speaker accommodated inside the housing, and an eartip that is mounted on the end portion side of the housing having the elasticity, and that includes a sound conduit portion through which sound from the speaker passes, and an elastic electrode that performs sensing of an electroencephalogram of a wearer.

An information processing device according to another aspect includes an acquiring unit that acquires an electroencephalogram signal, an estimating unit that estimates a state of a wearer from the acquired electroencephalogram signal, using a model that has learned a predetermined electroencephalogram signal of the wearer of the earphone and a state of the wearer at the time of acquiring the predetermined electroencephalogram signal, and a processing unit that performs processing on the basis of the state of the wearer that is estimated.

Advantageous Effects of Invention

According to one aspect of the present invention, an earphone can be provided in which electroencephalogram electrodes come into close contact more readily when worn. Also, according to another aspect of the present invention, the state of a wearer can be appropriately estimated from electroencephalogram signals using a model generated for the wearer.

DESCRIPTION OF EMBODIMENTS

Embodiments of the present invention will be described below with reference to the Figures. It should be noted however, that the embodiments described below are only exemplary, and do not intend to exclude application of various modifications and technologies not specified below. That is to say, the present invention can be variously modified and carried out without departing from the scope of the essence thereof. Also, in the description of Figures below, parts that are same or similar are denoted by the same or similar signs. The Figures are schematic, and do not necessarily match actual dimensions, proportions, or the like. The Figures may include portions in which dimensional relations or proportions differ thereamong.

First Embodiment

An example of earphones according to a first embodiment will be described below with reference to the Figures.
<Overview of Earphones>

Figure 1:
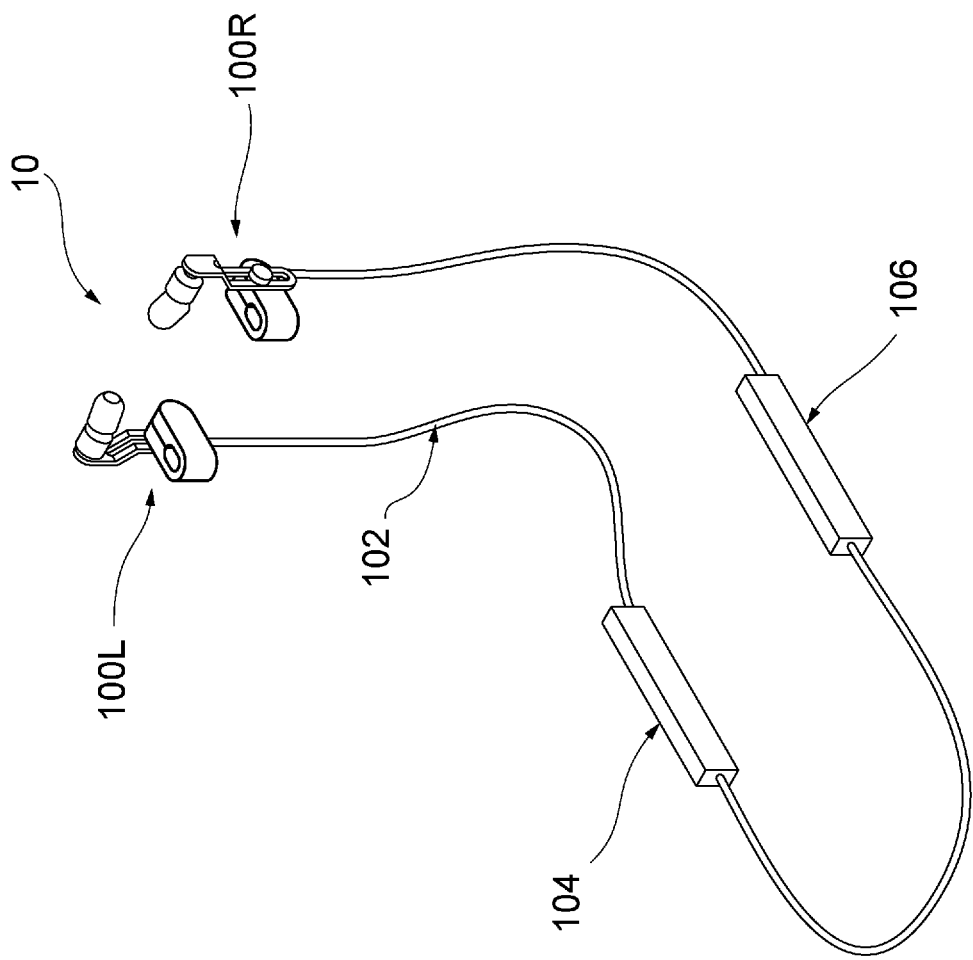
FIG. 1 is a diagram illustrating an overall example of an earphone set according to a first embodiment.
Figure 2:
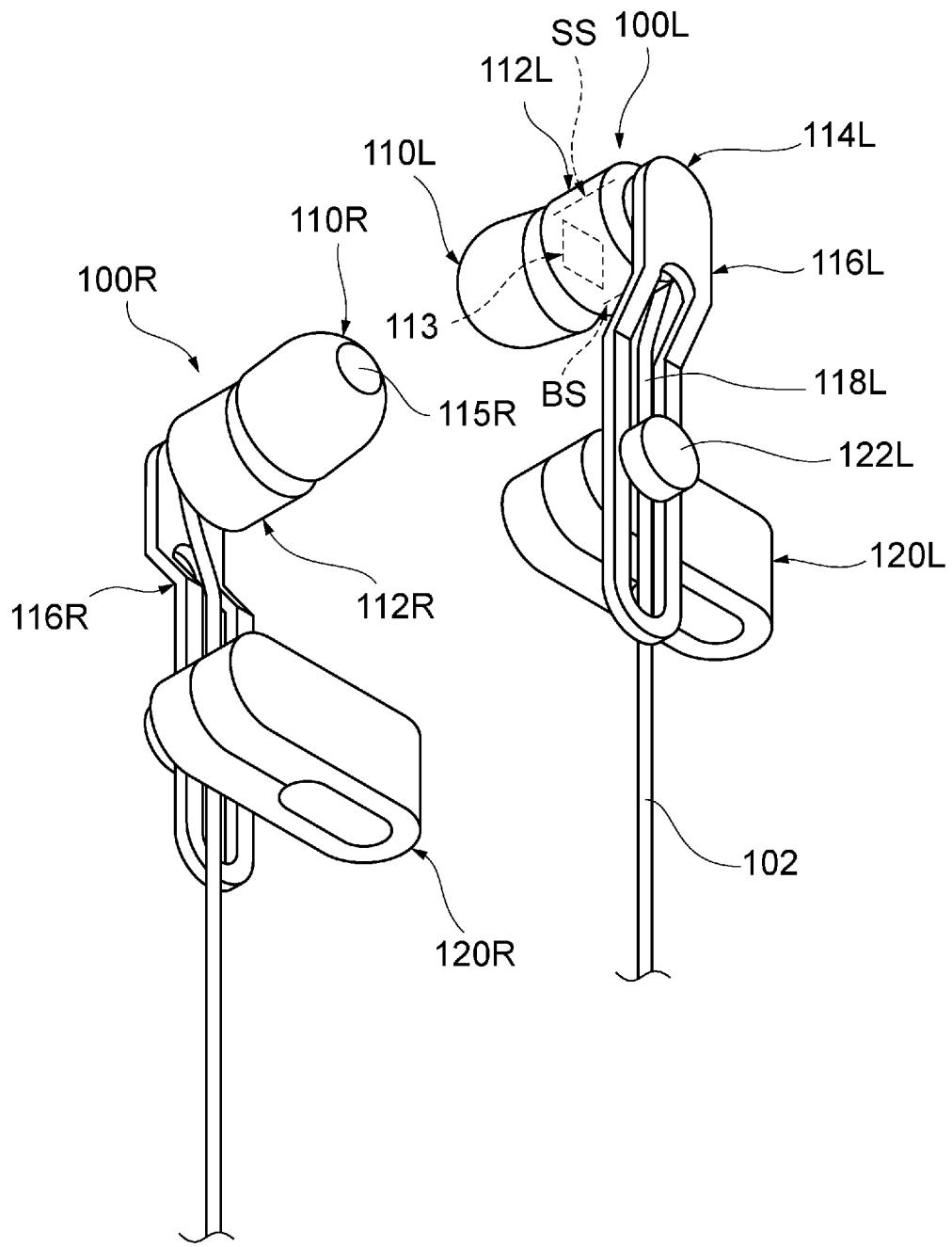
FIG. 2 is a diagram illustrating an enlarged example of an earphone portion according to the first embodiment.
Figure 3:
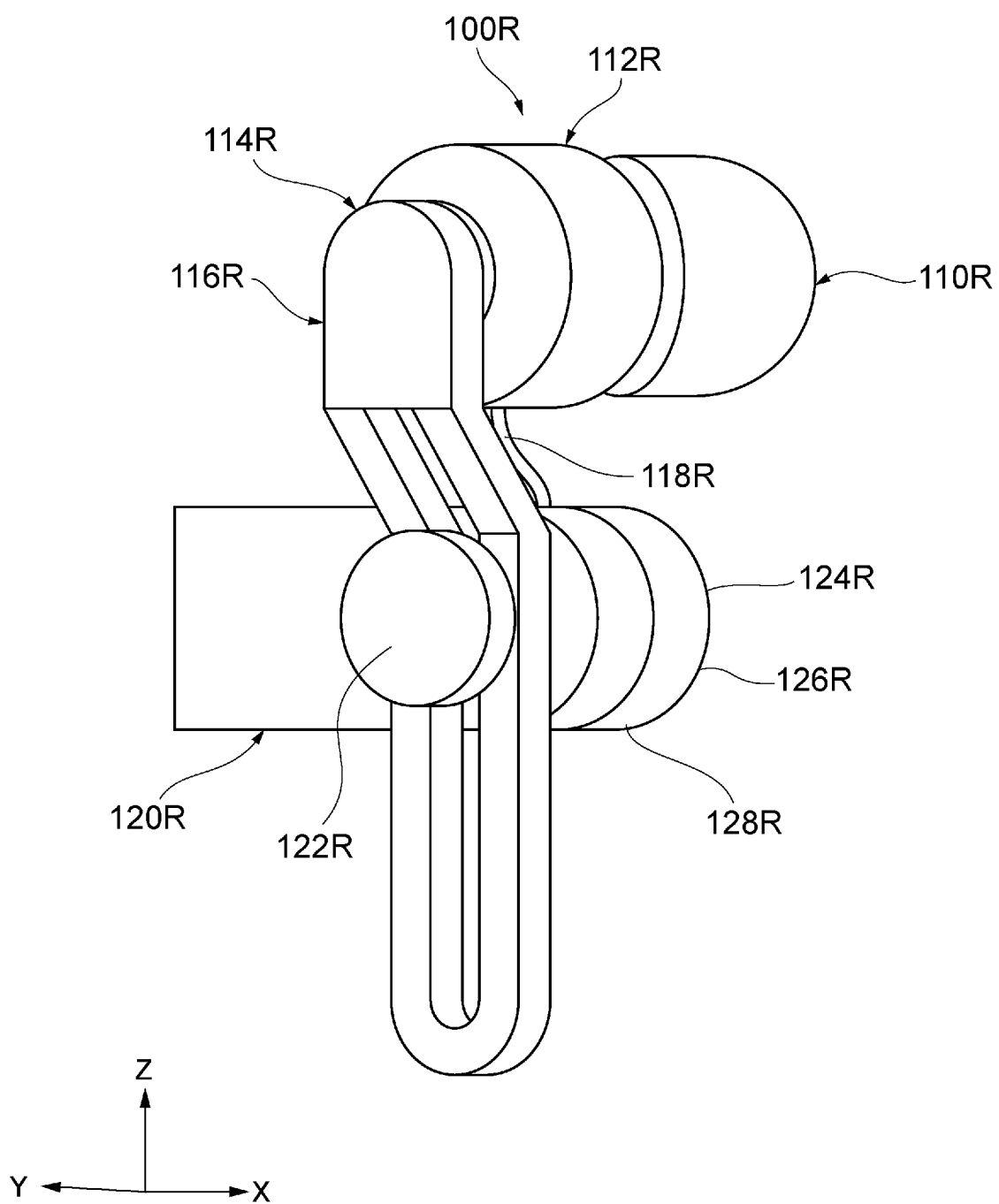
FIG. 3 is a diagram illustrating an example of a right portion of earphones according to the first embodiment.

First, an overview of the earphones according to the first embodiment will be described with reference to FIGS. 1 to 3. FIG. 1 is a diagram illustrating an overall example of an earphone set 10 according to the first embodiment. FIG. 2 is a diagram illustrating an enlarged example of an earphones 100 portion according to the first embodiment. FIG. 3 is a diagram illustrating an example of a right portion of earphones 100 according to the first embodiment. The earphone set may be referred to simply as earphones.

In FIGS. 1 to 3, the earphone set 10 includes a pair of earphones 100R and 100L, a cable 102 connected to each of the pair of earphones 100R and 100L, a first accommodation case 104, and a second accommodation case 106, which are provided at optional positions upon the cable 102. The first accommodation case 104 and the second accommodation case 106 may include, for example, a communication circuit (communication interface) for communication of audio signals with other devices, an operating unit having functions of operating the earphones 10, a power source (battery), a microphone, and so forth. The cable 102 may include, for example, a plurality of signal lines connecting circuits and so forth within the first accommodation case 104, the second accommodation case 106 and the earphones 100R (L).

Note that the first accommodation case 104 and the second accommodation case 106 may be integrated into one. Also, the earphones 10 may be configured as a wireless type that does not need the cable 102, by the circuits and so forth that is accommodated inside the first accommodation case 104 and the second accommodation case 106 being accommodated in a housing 112 of the earphones 10, as described later. Note that when the right (R) and left (L) of the configurations are not to be distinguished in particular, the R and L signs will be omitted.

The earphones 100 have eartips 110, the housings 112, speakers 113 accommodated inside the housings 112, joint mechanisms 114, connecting portions 116, cables 118, and gripping portions 120, as illustrated in FIGS. 2 and 3.

The eartips 110 are mounted on one end portion side of the housings 112. At this time, the one end portion side of the housings 112 is formed of a material having flexibility, such as an elastic material, a rubber material, or the like, for example. This is to keep the vibrations of the housings 112 from being conveyed to the eartips 110. The eartips 110 also include sound conduit portions 115 through which sound passes from the speakers 113 accommodated inside the housings 112, and elastic electrodes that perform sensing of electroencephalograms of the wearer. The elastic electrodes are configured of all or part of the eartips 110, for example, and rubber electrodes capable of acquiring biosignals or the like can be used. Accordingly, the eartips 110 including the elastic electrodes can acquire the electroencephalogram signals of the wearer by coming into close contact with the inner walls of the ear canals.

The eartips 110 are detachably attached to nozzles protruding from one end portion of the housings 112. The sound conduit portions 115 function as channels through which sound from the speakers 113 passes. The nozzles also have therein sound conduit portions through which sound output from the speakers 113 passes, and the sound passes through the sound conduit portions 115 of the eartips 110 partially overlapping the sound conduit portions of the nozzles and reaches the eardrums of the wearer. Also, the elastic electrodes included in the eartips 110 and copper lines (later-described first signal lines) within the housings 112 are provided at positions as far away from the sound conduit portions 115 as possible. For example, the elastic electrodes are provided on the outer edges of the eartips 110, and the copper lines are provided at the outer edges within the housings 112. Accordingly, the elastic electrodes and the copper lines that transmit the electroencephalogram signals are less readily affected by vibrations of sound.

The housings 112 have elasticity on at least one end portion side outer layer. The nozzles protrude at the end portion sides having elasticity, and the eartips 110 are mounted to these nozzles. Accordingly, when the earphones 10 are inserted into the ear canals, the elastic portions of the eartips 110 and the housings 112 are mounted being elastically deformed in accordance with the shape of the ear canals of the wearer, and thus the elastic portions of the eartips 110 and the housings 112 are fit into the inner walls of the ear canals of the wearer. As a result, the elastic electrodes of the eartips 110 fit into the inner walls of the ear canals can acquire electroencephalogram signals with good precision.

As least one end portion of the housings 112 has elasticity and flexibility, as described above. The material from which the housings 112 are made is not limited as long as the material has such characteristics. One example thereof is a material that is soft, low-resistance, and sturdy, such as silicone rubber, for example. The housings 112 are elastically deformable under human strength. The nozzles are configured to be adjustable so that the direction of extension thereof follows the ear canals due to the elastic deformation of the housings 112.

For example, when putting on the earphones 10, the end portions of the housings 112 that have elasticity first come into contact with the outer ear, and are deformed so as to be depressed, yielding to the contact pressure. When the earphones 10 are worn, the eartips 110 including the elastic electrodes are positioned in the ear canal, and are in close contact with the entire circumference of the ear canal.

Also, the housings 112 have storage spaces in the opposite direction from the nozzles, with circuit boards including sound processing circuits and the speakers 113 in the storage spaces. It is sufficient for the speakers 113 to be disposed within the housings 112 with consideration given such that the directionality of output sound of the speakers 113 directly heads toward the eardrums within the ear canals, for example. As an example, the speakers 113 are disposed so that sound is output from the middle portions of the housings 112. Also, the peripheral portions of the speakers 113 are covered with a cushioning material such as a foamed material or the like, so that the housings 112 and the speakers 113 do not come into direct contact due to this cushioning material. Accordingly, vibrations are not readily conveyed to the housings 112 when sound is output from the speakers 113, and vibrations are not readily conveyed to the sensors (elastic electrodes) of the eartips 110 via the housings 112. That is to say, the effects of vibrations accompanying output of sound can be reduced when sensing electroencephalogram signals.

The joint mechanisms 114 are mechanisms that connect end portions of the housings 112 on the opposite side from the nozzles and the connecting portions 116. For example, the joint mechanisms 114 are ball-joint mechanisms by which at least the housings 112 can be rotated in a horizontal direction (direction of the XY plane) to perform adjustment. Also, the joint mechanisms 114 may enable the housings 112 to rotate 360 degrees, such that the positions of the housings 112 are adjustable.

Accordingly, electroencephalogram signals can be appropriately acquired by adjusting the positions of the housings 112 by the joint mechanisms 114 and bringing the eartips 110 that have the elastic electrodes into close contact with the inner walls of the ear canals, in accordance with the shapes of ears that differ from one user to another.

The connecting portions 116 are mechanisms that connect the housings 112 and the gripping portions 120. The connecting portions 116 have rigidity and are made of resin or the like, for example. The connecting portions 116 also extend in a predetermined direction, e.g., following a vertically downward direction, from a position at which the connecting portions 116 are fixed to the housings 112. The extending portions may have curved shapes coming closer to the eartips 110 sides.

The cables 118 internally include the first signal lines that transmit sensing signals from the elastic electrodes of the eartips 110 to processing circuits 144 (see FIGS. 4 and 5) within the gripping portions 120, and second signal lines that connect the circuit boards within the housings 112 and a communication circuit 150 (see FIGS. 4 and 5) for transmitting sound. Note that the second signal lines may each be a plurality of signal lines.

The gripping portions 120 grip the earlobes of the wearer, and have electrodes in the peripheral regions of the end portions. For example, the gripping portions 120 have second electrodes 140 on one end portion and third electrodes 142 on the other end portion. The second electrodes 140 are grounding electrodes, and the third electrodes 142 are electrodes that function as reference electrodes. In this case, electroencephalogram signals can be acquired with good precision by calculating the difference between signals sensed by the elastic electrodes (first electrodes) of the eartips 110 and the signals sensed by the third electrodes that are reference electrodes. This is because signals acquired from the earlobe portions contain almost no electroencephalogram signals.

Also, the gripping portions 120 have configurations for pinching the earlobes, having clip-like configurations, for example. Also, the gripping portions 120 are preferably configured of a material having elasticity such as rubber, to gently fit to the earlobes. Note that the gripping portions 120 do not necessarily have to be configurations that pinch the earlobes, and it is sufficient to have plate-like configurations that can suitably come into contact with the earlobe portions.

Also, the gripping portions 120 may include converters that convert electroencephalogram signals acquired on the basis of the elastic electrodes (first electrodes) into digital signals. The converters process, and convert into digital signals, the electroencephalogram signals sensed at a predetermined sampling rate, for example. Accordingly, shortening the length of signal lines transmitting analog electroencephalogram signals enables noise to be included less readily, the electroencephalogram signals to be quickly digitized, and noise immunity to be raised.

Also, the end portions of the gripping portions 120 may have magnets. For example, a positive-pole magnet is provided to one end portion, and a negative-pole magnet is provided to the other end portion. Accordingly, appropriate pressure contact with the earlobes can be realized when bringing the second electrodes and the third electrodes into contact with the earlobes, and the burden on the ears can be mitigated.

Also, the connecting portions 116 may have adjustment mechanisms by which the positions of the gripping portions 120 are adjustable. For example, the adjustment mechanisms are sliding mechanisms, having mechanisms that move the positions of the gripping portions 120 up and down in a Z direction (vertical direction, or direction connecting the chin of the face and the top of the head). The adjustment mechanisms may also have mechanisms capable of fixing the gripping portions 120 following the predetermined direction in which the connecting portions 116 extend.

This enables the positions of the gripping portions 120 to be adjusted in accordance with the shape and size of the earlobes that differ from one user to another, bringing the reference electrodes into contact at appropriate positions enables signals to be acquired from the reference electrodes more appropriately.

Note that the adjustment mechanisms are not limited to sliding mechanisms, and any mechanisms may be employed as long as the positions of the gripping portions 120 are adjustable. For example, the connecting portions 116 may be configured having a plurality of holes in a predetermined direction, with the gripping portions 120 being fixed by fitting protrusions on the gripping portions 120 into the holes. Also, the connecting portions 116 may have fixing members 122 for fixing the connecting portions 116 after moving the gripping portions 120. For example, the fixing members 122 bring the gripping portions 120 into pressured contact with the connecting portions 116 by rotating, and fix the gripping portions 120. As a specific example, the fixing members 122 have screw portions (bolts) extending in the direction of the gripping portions 120 and the gripping portions 120 have nuts that receive the screw portions of the fixing members 122.

<Configuration of Gripping Portions>

Figure 4:
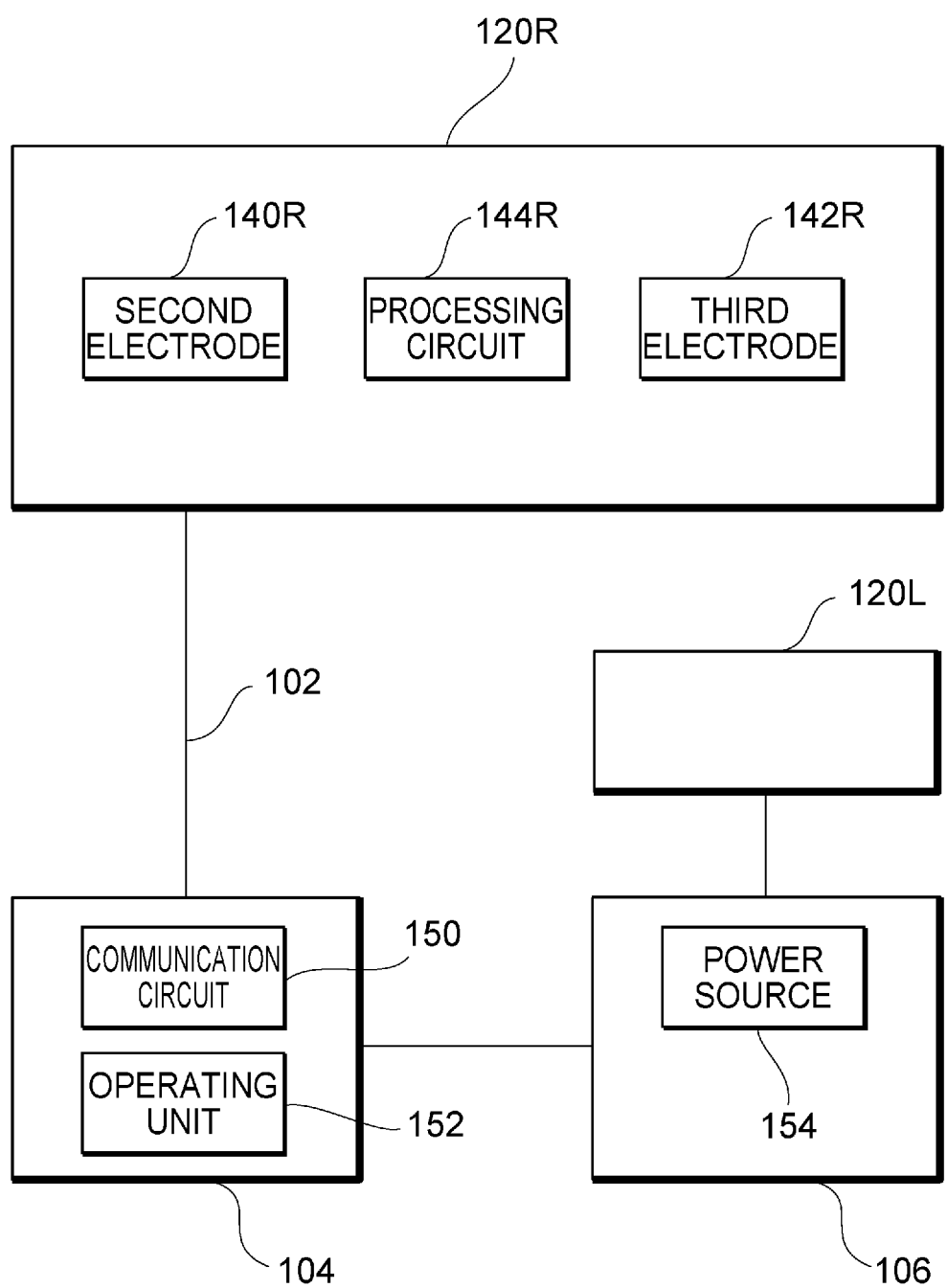
FIG. 4 is a diagram illustrating an example of a configuration of a gripping portion according to the first embodiment.
Figure 5:
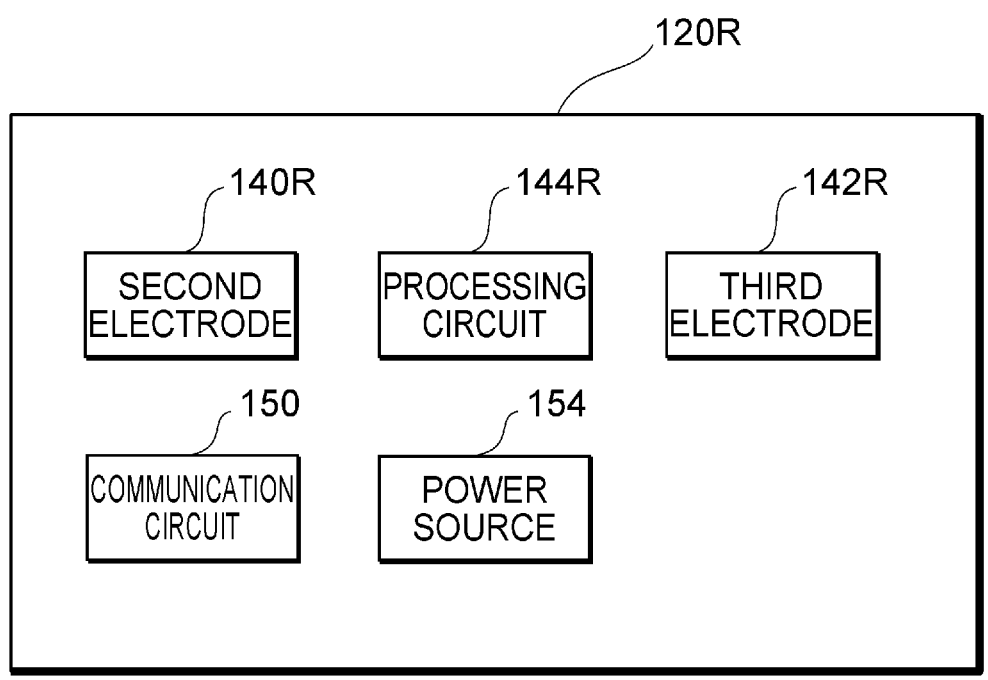
FIG. 5 is a diagram illustrating an example of a configuration of the gripping portion according to the first embodiment.

FIGS. 4 and 5 are diagrams illustrating an example of the configuration of the gripping portions 120 according to the first embodiment. FIG. 4 illustrates the configuration of the gripping portion 120 in a case of wireless-type earphones 10, and FIG. 5 illustrates the configuration of the gripping portion 120 of wireless-type earphones 10.

As illustrated in FIG. 4, a gripping portion 120R has a second electrode 140R, a third electrode 142R, and a processing circuit 144R. As described above, the second electrode 140R is a grounding electrode, and the third electrode 142R is an electrode functioning as a reference electrode. The second electrode 140R and the third electrode 142R may be elastic electrodes. For example, the gripping portion 120R suitably is a plate-shaped member that has a configuration of bending around the middle in the longitudinal direction of the plate-shaped member, and at least the portion thereof that comes into contact with the ear, such as the earlobe or the like, has elasticity. The gripping portions 120 come into contact with the earlobes by pinching the earlobes, by bending around the middle.

The processing circuit 144R includes a signal processing circuit that converts electroencephalogram signals sensed by the elastic electrode of the eartip 110 into digital signals. Also, a gripping portion 120L has the same configuration as the gripping portion 120R.

The first accommodation case 104 includes the communication circuit 150 and an operating unit 152. The communication circuit 150 includes an antenna for performing wireless communication. The antenna conforms to a wireless communication standard such as Bluetooth (registered trademark), for example. Accordingly, the earphones 10 are wirelessly connected to equipment such as a mobile terminal, laptop, or the like, and perform communication of sound data with such equipment. The operating unit 152 has operating functions for controlling the sound processing circuit within the housing 112 regarding volume and playback.

The second accommodation case 106 has a power source 154, and the power source 154 supplies electric power to the circuits and so forth. The second accommodation case 106 also has a charging opening, for example, through which charging of the power source 154 is performed. The cable 102 has a signal line, and transmits signals to the circuits. Note that the configuration illustrated in FIG. 4 is an example, and the parts may be configured to be accommodated in any accommodation case.

FIG. 5 illustrates a wireless-type earphones 10, illustrating an example in which the configurations accommodated in the accommodation case in FIG. 4 are accommodated in the gripping portion 120. As illustrated in FIG. 5, the gripping portion 120R has the second electrode 140R, the third electrode 142R, the processing circuit 144R, the communication circuit 150, and the power source 154. The functions of each part are the same as the contents illustrated in FIG. 4.

This enables a wireless type to be realized, the cable 102 and the accommodation cases become unnecessary, and the reduction in the number of parts for manufacturing the earphones 10 enables manufacturing costs to be reduced.

Also, the example illustrated in FIG. 5 is only an example, and the parts may be provided in the housings 112. For example, the communication circuit 150 and the processing circuits 144 may be provided in the housings 112. Also, the configurations inside the housings 112 and the configurations inside the gripping portions 120 can be decided taking into consideration the burden on the ears.

According to the earphones 10 of the first embodiment described above, the housings 112 having elasticity can be deformed in accordance with the size and shape of the concha of the ear when worn by the wearer, and accordingly the eartips 110 having the elastic electrodes enter following the ear canals, and the eartips 110 come into close contact with the entire circumference of the ear canal. As a result, electroencephalogram signals from the elastic electrodes can be appropriately sensed.

Also, all exterior portions of the earphones 10 that come in contact with skin (the housings 112) may be formed of a material having elasticity and flexibility, not just the eartips 110. Accordingly, even though there may be personal differences in ear shapes and so forth, closely fitting the earphones 10 to the ears enables a high level of wearing comfort, a high level of sound insulation, and difficulty of becoming dislodged, to be obtained, while also enabling electroencephalogram signals to be acquired appropriately.

Second Embodiment

An example of an electroencephalogram signal processing system according to a second embodiment will be described below with reference to the Figures.

System Application Example

Figure 6:
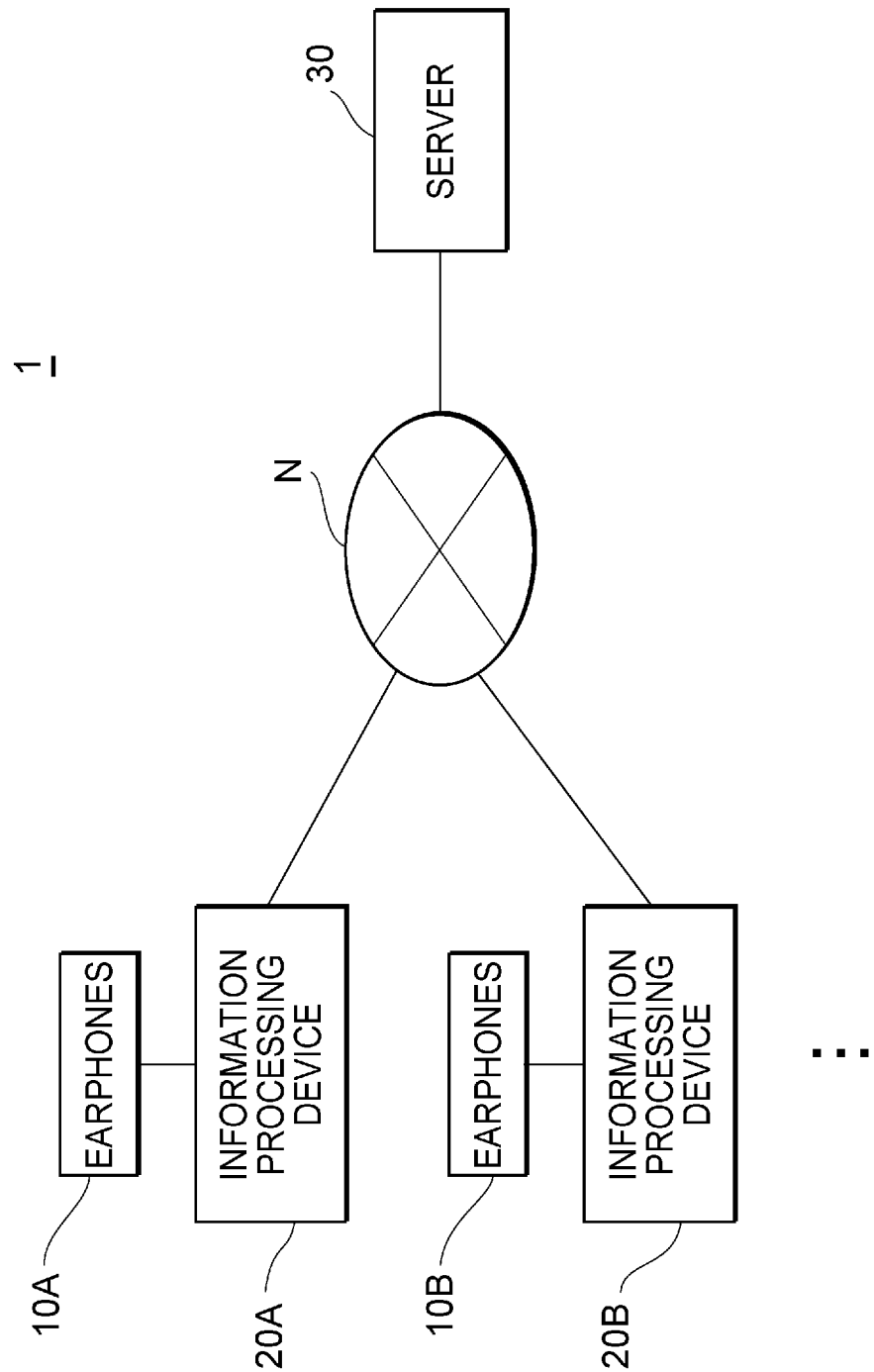
FIG. 6 is a diagram illustrating configuration examples of an electroencephalogram signal processing system according to a second embodiment.

FIG. 6 is a diagram illustrating configuration examples of an electroencephalogram signal processing system 1 according to the second embodiment. In the example illustrated in FIG. 6, earphones 10A, 10B, . . . , used by users, information processing devices 20A, 20B, . . . , and a server 30 that processes electroencephalogram signals, are connected via a network N. Note that the English symbols such as A and B will be omitted when individual configurations are not being distinguished.

The earphones 10 are the earphones 10 described in the first embodiment, but are not necessarily limited to this. The earphones 10 acquire at least one electroencephalogram signal from each of the left and right earphones 1 OR and 10L, and acquire a total of two electroencephalogram signals. Note that there is no need for the number of electroencephalogram signals to be two. Also, the earphones 10 are not limited to being earphones, and any device that can sense electroencephalograms is sufficient.

The information processing device 20 is, for example, a smartphone, a cellular phone (feature phone), a computer, a tablet terminal, a PDA (Personal Digital Assistant), and so forth. The information processing device 20 is also written as user terminal 20.

An information processing device 30 is a server for example, and may be configured of one or a plurality of devices. Also, the information processing device 30 processes electroencephalogram signals, and analyzes states of users from electroencephalogram signals by using learning functions of artificial intelligence (AI), for example. The information processing device 30 is also written as server 30.

In the example illustrated in FIG. 6, a user (user A) using a user terminal 20A wears the earphones 10A, and the earphones 10A acquire electroencephalogram signals of the user A. The earphones 10A transmit the electroencephalogram signals of the user A to the user terminal 20, and the electroencephalogram signals are processed by an application in the user terminal 20. At this time, the application may analyze the electroencephalogram signals using edge AI, or transmit the electroencephalogram signals to the server 30 and acquire analysis results from the server 30. The application provides the user A with the state of the user A that is estimated using the electroencephalogram signals, training for transitioning from the current state based on the electroencephalogram signals to a predetermined state, and so forth.

Example of Configuration

Figure 7:
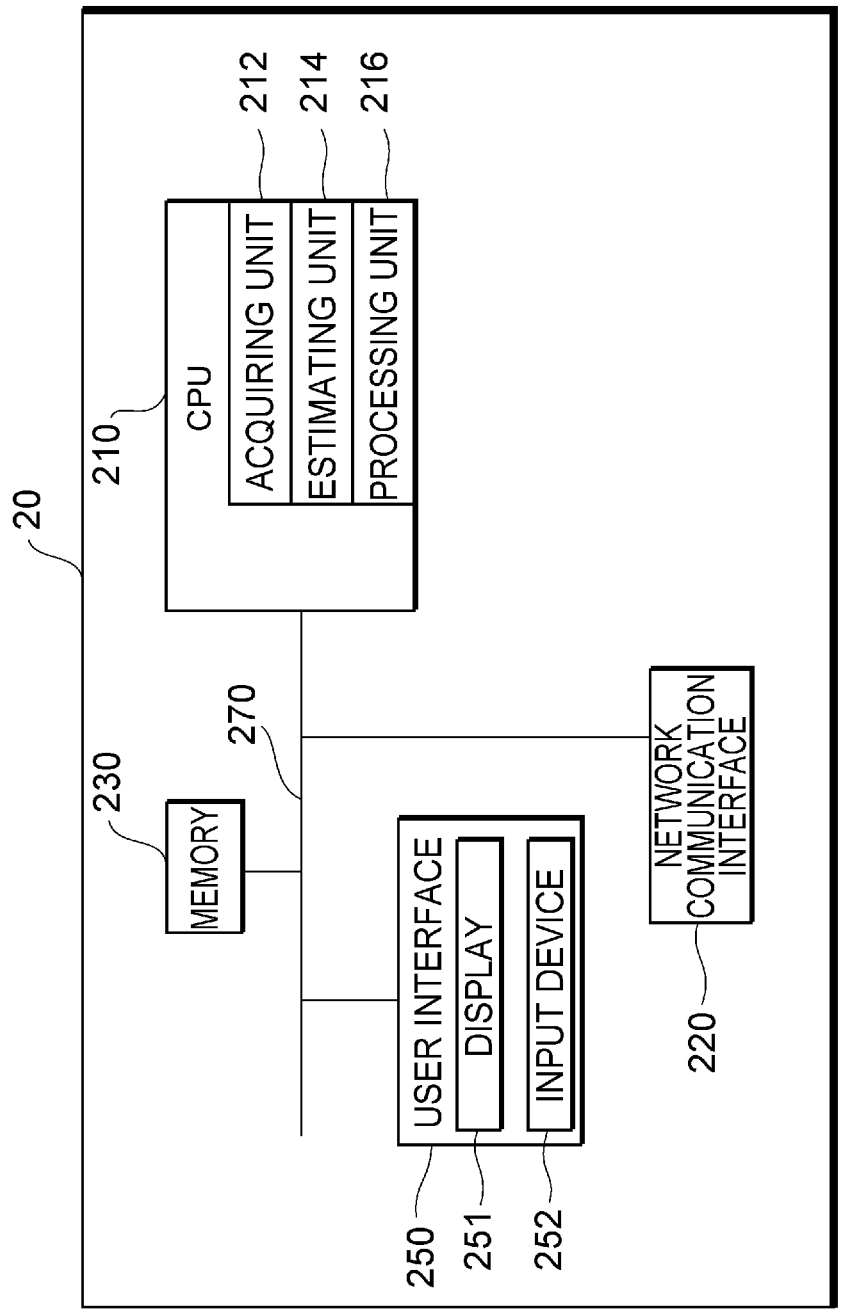
FIG. 7 is a block diagram illustrating an example of a user terminal according to the second embodiment.

FIG. 7 is a block diagram illustrating an example of the user terminal 20 according to the second embodiment. The user terminal 20 includes one or a plurality of processing devices (control unit: CPU) 210, one or a plurality of network communication interfaces 220, memory 230, a user interface 250, and one or a plurality of communication busses 270 connecting these components to each other.

The user interface 250 includes, for example, a display device 251 and an input device (a keyboard and/or a mouse or some other pointing device or the like) 252. The user interface 250 may also be a touch panel.

The memory 230 is high-speed random-access memory such as, for example, DRAM, SRAM, DDR RAM, or some other random-access solid-state memory device, and may be non-volatile memory such as one or a plurality of magnetic disk storage devices, optical disc storage devices, flash memory devices, or some other non-volatile solid-state storage device.

Also, another example of the memory 230 may be one or a plurality of storage devices installed remotely from the CPU 210. In one embodiment, the memory 230 stores the following program, module, and data structure, or a subset thereof.

The one or a plurality of processing devices (CPU) 210 read out programs from the memory 230 and execute the programs, as necessary. For example, the one or plurality of processing devices (CPU) 210 may make up an acquiring unit 212, an estimating unit 214, and a processing unit 216, by executing a program stored in the memory 230.

The acquiring unit 212 acquires electroencephalogram signals output from the earphones 10 via the network communication interfaces 220.

The estimating unit 214 estimates the state of the wearer from the acquired electroencephalogram signals, using a model that has learned predetermined electroencephalogram signals of the wearer of the earphones 10 and the state of the wearer at the time of acquiring these predetermined electroencephalogram signals. The model used here is a trained model customized to the characteristics of the individual brain of the wearer, using electroencephalogram signals of the wearer him/herself. For example, this trained model is a model including an inference program that is trained regarding electroencephalogram signals using training data in which information that the wearer has instructed as being the state (e.g., state defined by valence (Positive/Negative) and arousal (Arousal Level), etc.) of the wearer him/herself at the time of acquiring electroencephalogram signals is correct labels, and that infers the state of the wearer from the electroencephalogram signals. The trained model may also be a model learned by the server 30.

The processing unit 216 performs processing on the basis of the state of the wearer estimated by the estimating unit 214. This enables processing in accordance with the state of the wearer estimated from the electroencephalogram signals of the wearer using a model trained for the wearer, and outputting processing results customized for the individual, and so forth, is enabled.

The trained model may be a customized model in which a predetermined model, which is trained regarding electroencephalogram signals of another person and the state of the other person at the time of acquiring these electroencephalogram signals, has additionally learned the electroencephalogram signals of the wearer and the state of the wearer at the time of acquiring the electroencephalogram signals. Accordingly, a certain level of estimation capabilities can be had at an initial stage, and personal customization can be performed as usage (learning) advances.

The processing unit 216 may perform induction processing for inducing transition from the state of the wearer estimated on the basis of the current electroencephalogram signals to a predetermined state of the wearer indicated by first electroencephalogram signals, in which induction processing, feedback to the wearer is performed on the basis of the current electroencephalogram signals. For example, the processing unit 216 causes the wearer to instruct a better state, by causing the wearer to view and listen to various types of contents when using the earphones 10. For example, the processing unit 216 causes the wearer to instruct good states such as preferable, concentration-enabling, relaxing, slumberous, and so forth. The contents are, for example, music, videos, games, and so forth. As for the way in which instruction is performed, the processing unit 216 displays UI parts (icons, buttons, etc.) indicating a good state on the screen of the user terminal 20, and the user operates the UI parts when in a good state, for example. Note that the contents are imparted labels representing characteristics, such as genres. For example, in a case in which the contents are videos, the labels include kids, family, documentary, comedy, suspense, romance, action, and so forth, in a case in which the contents are music, the labels include rock, pops, ballads, classical, and so forth. The labels may be the type or atmosphere of works. The types of works include cerebral works, violent works, works that all can enjoy, controversial works, dark works, works that make people happy, family-oriented works, witty works, and so forth. The atmosphere of works include tender works, wild works, and so forth.

Figure 8:
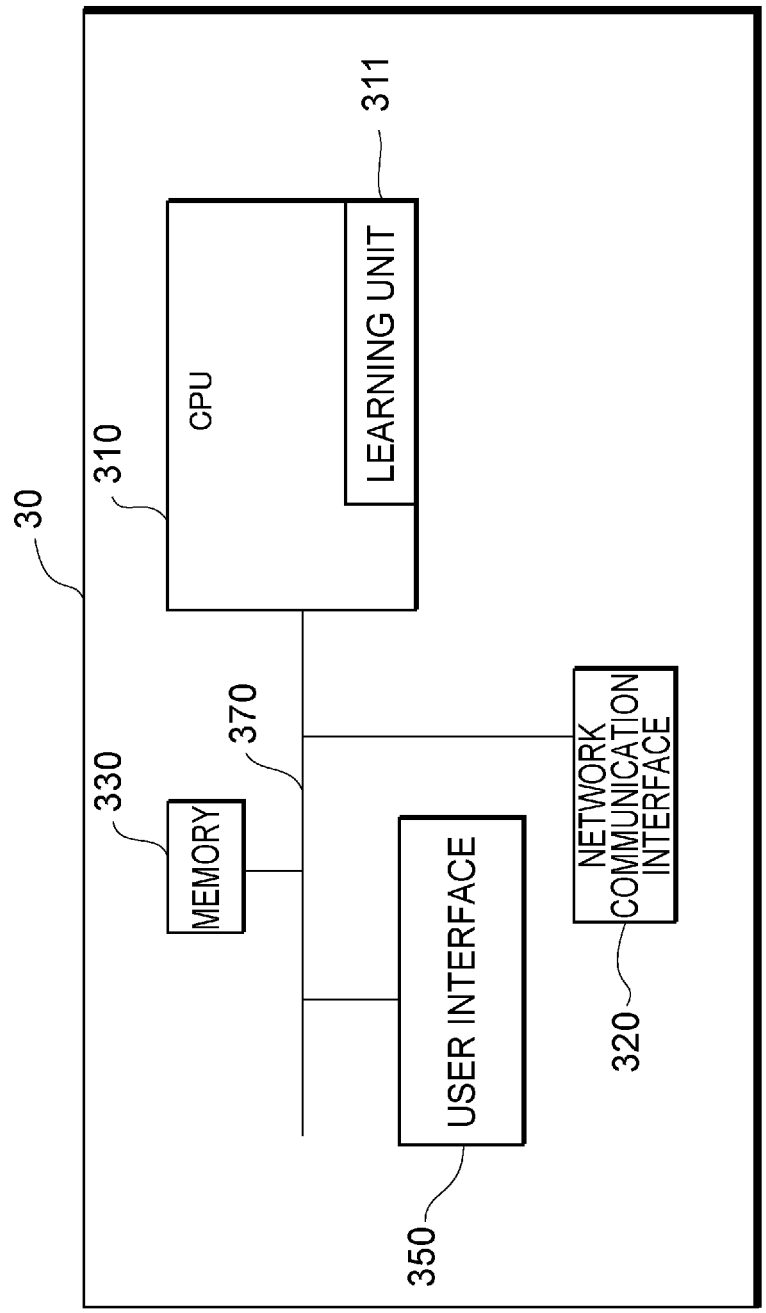
FIG. 8 is a block diagram illustrating an example of a server according to the second embodiment.

The processing unit 216 correlates the waveforms and characteristics of electroencephalogram signals when the wearer has instructed a good state thereof (first electroencephalogram signals) with characteristics of the contents, and use these as training data to train a learning unit 311 of the server 30 (see FIG. 8). By training the learning unit 311 of the server 30 with the electroencephalogram signals before and after transitioning to the first electroencephalogram signals when in a good state of the wearer, states at the time of the respective electroencephalogram signals, and characteristics of the contents, as training data, the processing unit 216 can perform training regarding watching what sort of videos, listening to what sort of music, and playing what sort of games, will cause transition to a good state, and generate a trained model including an inference algorithm.

By learning the electroencephalogram signals and state before and after transitioning to this good state, and the contents, the processing unit 216 can comprehend what sort of contents the wearer should be presented with in order to transition from the current electroencephalogram signals of the wearer to a good state for the wearer. The processing unit 216 notifies the wearer of the analysis results using the trained model, as feedback results.

FIG. 8 is a block diagram illustrating an example of the server 30 according to the second embodiment. The server 30 includes one or a plurality of processing devices (CPU) 310, one or a plurality of network communication interfaces 320, memory 330, and one or a plurality of communication busses 370 for connecting these components to each other.

The server 30 may include a user interface 350 depending on the case, examples thereof including a display device (omitted from illustration), and a keyboard and/or a mouse (or an input device such as some other pointing device or the like. Omitted from illustration).

The memory 330 is high-speed random-access memory such as, for example, DRAM, SRAM, DDR RAM, or some other random-access solid-state memory device, and may be non-volatile memory such as one or a plurality of magnetic disk storage devices, optical disc storage devices, flash memory devices, or some other non-volatile solid-state storage device.

Also, another example of the memory 330 may be one or a plurality of storage devices installed remotely from the CPU 310. In one embodiment, the memory 330 stores the following program, module, and data structure, or a subset thereof.

The one or a plurality of processing devices (CPU) 310 reads out programs from the memory 330 and executes the programs, as necessary. For example, the one or plurality of processing devices (CPU) 310 may make up the learning unit 311 by executing a program stored in the memory 330.

The learning unit 311 analyzes the state of the wearer using the electroencephalogram signals of the wearer, and generates a model (first model). For example, a model in which an optional extracting method out of a plurality of techniques for extracting training data from electroencephalogram signals, and an optional classifier out of a plurality of classifiers, are combined, or the like, may be used. The extracting method includes wavelet transform, Fourier transform, and so forth, and examples of the classifier include random forest (Random Forest), support-vector machine (SVM: Support Vector Machine), neural network, decision tree, and so forth.

<Feedback Training>

It is known that frequency and potential tendencies of electroencephalograms differ from one individual to another. Accordingly, a user individual of which an electroencephalogram is being measured is caused to perform annotation of an optional state of him/herself (e.g., first state), using symbols, emoticons, and so forth, displayed on the user terminal 20. Thus, by learning the electroencephalogram signals and the annotations, the learning unit 311 becomes capable of predicting and visualizing the first electroencephalogram signals corresponding to the first state and transition from optional electroencephalogram signals to the first electroencephalogram signals. Also, the user seeks to reproduce an optional state by performing predetermined training so as to transition from optional electroencephalogram signals to the first electroencephalogram signals.

The processing unit 216 calculates frequency bands for performing electroencephalogram training, for each wearer individual. For example, the processing unit 216 detects an Individual Alpha frequency Peak (IAP) from the electroencephalogram signals. The processing unit 216 then sets the frequency bands of delta (0.5 to 3 Hz), theta (4 to 7 Hz), alpha (8 to 13 Hz), beta (14 to 30 Hz), and gamma (30 Hz and higher), around the IAP, for each individual. The processing unit 216 finds the ratio between the total potential (e.g., average value of all frequency bands) of the electroencephalogram signals, and the potential for each frequency band (e.g., average value of each frequency band). Alpha waves are said to appear when at rest, awakening, and closing eyes, and theta waves, delta waves, and so forth, are set with the alpha waves as a reference.

The processing unit 216 also calculates a predetermined ratio (hereinafter, "golden ratio") for each wearer individual. As a calculation method of the golden ratio, the electroencephalogram signals when in an optional good state are calculated for the wearer individual on the basis of analysis results by artificial intelligence (AI) by the server 30, divided into the frequency bands using predetermined Hz in a low-frequency direction and predetermined Hz in a high-frequency direction and so forth, around the IAP, and the ratio between an average value of all frequency bands and an average value or representative value of each frequency band is calculated. The representative value of each frequency band may be a peak frequency that has the highest value in each frequency band, or the like, for example. Also, the golden ratio may be the ratio of the average value or representative value of each frequency band.

Figure 9:
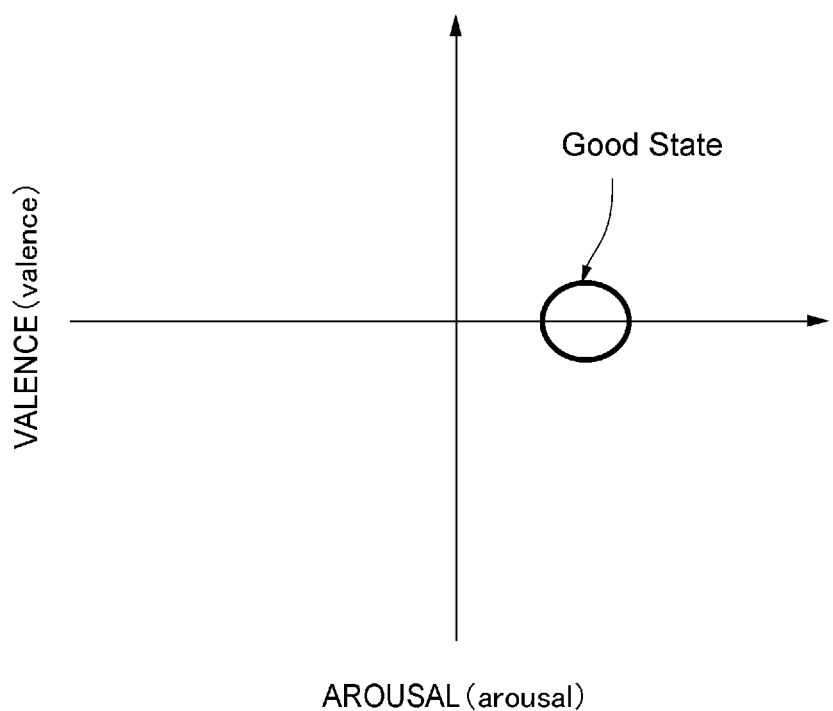
FIG. 9 is a diagram showing an example of a good state according to the second embodiment.

FIG. 9 is a diagram showing an example of a good state according to the second embodiment. The example shown in FIG. 9 shows a good state of one wearer, and there is a possibility that this may be at a different position in a case of another user. Good states may be identified by instructions from wearers. Instruction from a wearer is, for example, pressing a UI part indicating being in a good state on the screen of the user terminal 20 during sensing of electroencephalogram signals, or the like.

The processing unit 216 converts into ratios of average values or representative values of each frequency band in the electroencephalogram signals in the calculated good state. For example, the processing unit 216 may calculate a standard deviation of a ratio of electroencephalogram signals categorized by gender, age, and time, using electroencephalogram signals of various wearers, and may convert into a golden ratio for each band appropriate for each individual taking into consideration the calculated standard deviation and the golden ratio for that individual.

<Training Method>

1: The learning unit 311 analyzes frequency characteristics of the individual with the calculated IAP as a reference, and records the tendencies of potential.
2: The learning unit 311 learns features of the electroencephalogram signals of the individual in an optional state (not limited to a good state, and may be various states, such as concentrated, relaxed, and so forth), by annotation by the wearer.
3: The state of the individual can be estimated from electroencephalogram signals by the AI in the learning unit 311 sufficiently learning the features of the electroencephalogram signals.
4: The processing unit 216 uses the features of the electroencephalogram signals that have become estimable, to convert into frequency or potential.
5: The processing unit 216 performs training so as to come closer to a certain optional state of the individual that has been learned, e.g., so as to come closer to the numerical value of the frequency or potential that has been converted.
6: In this case, selection of a desired state may be optionally performed by the wearer, but may be automatically selected by the system.

7: The tunes or audio-visual to be used in the training at this time are automatically selected or recommended by the system in accordance with past training history.

8: After training, the processing unit 216 causes the wearer to perform annotation again regarding the effects thereof, and performs verification.

Figure 10:
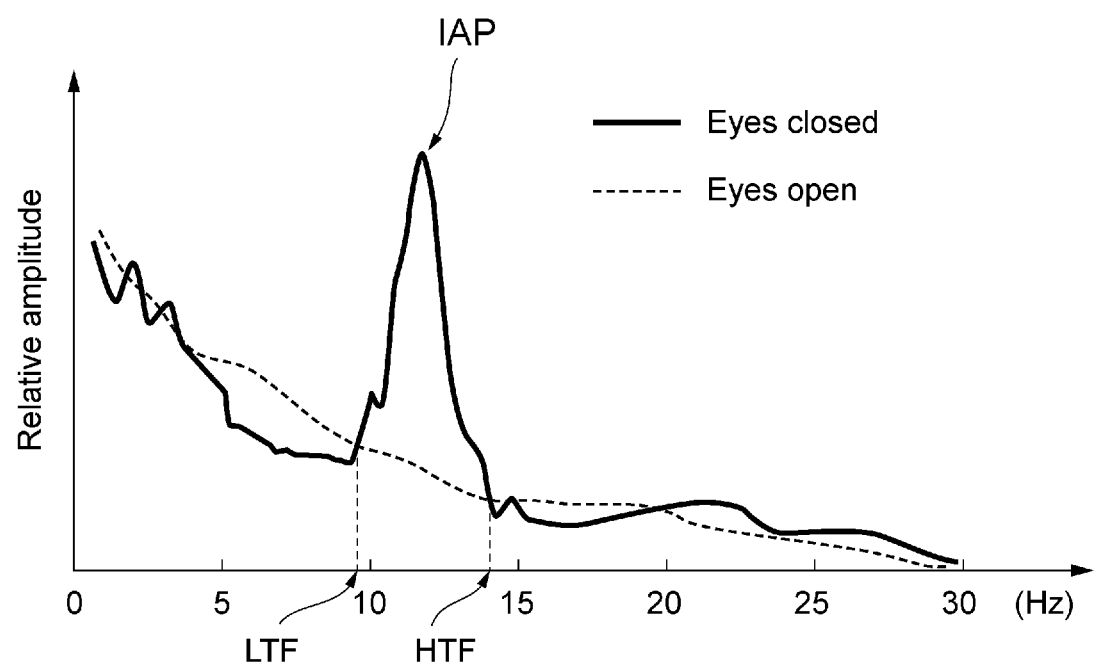
FIG. 10 is a diagram showing an example of a training band in which IAP is a reference, according to the second embodiment.

FIG. 10 is a diagram showing an example of a training band with an IAP as a reference, according to the second embodiment. The example in FIG. 10 shows an IAP of one wearer, and the IAP may be situated at a different frequency in a case of another wearer. Accordingly, in training using electroencephalogram signals for each individual, a training band is preferably set for each individual as shown in FIG. 10.

<Feedback>

The processing unit 216 selects contents and stimuli while giving feedback. The processing unit 216 selects music, videos, and so forth, which are optimal in guiding to an ideal potential state. For example, the processing unit 216 may generate recommendations from viewing and listening history of tunes and videos (individual, overall).

Figure 11:
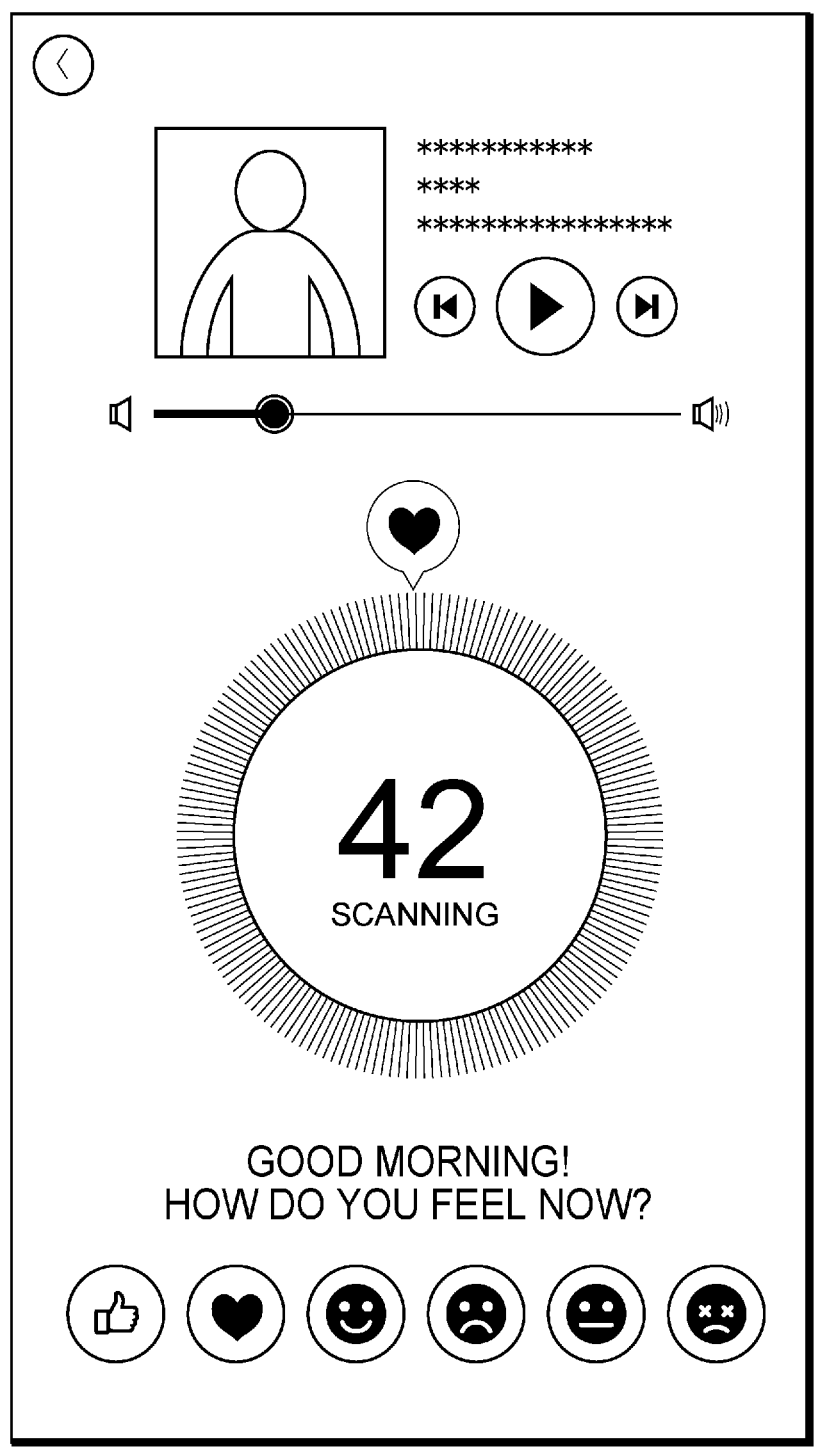
FIG. 11 is a diagram illustrating an example of a training screen according to the second embodiment.

Also, the processing unit 216 selects stimuli of audio-video for guiding to an optional potential state. For example, the processing unit 216 may generate recommendations from training history (individual, overall). FIG. 11 is a diagram illustrating an example of a training screen according to the second embodiment. As illustrated in FIG. 11, the wearer presses a face mark indicating the mood at that time while listening to music, whereby the state of the wearer can be learned.

<Operations>

Figure 12:
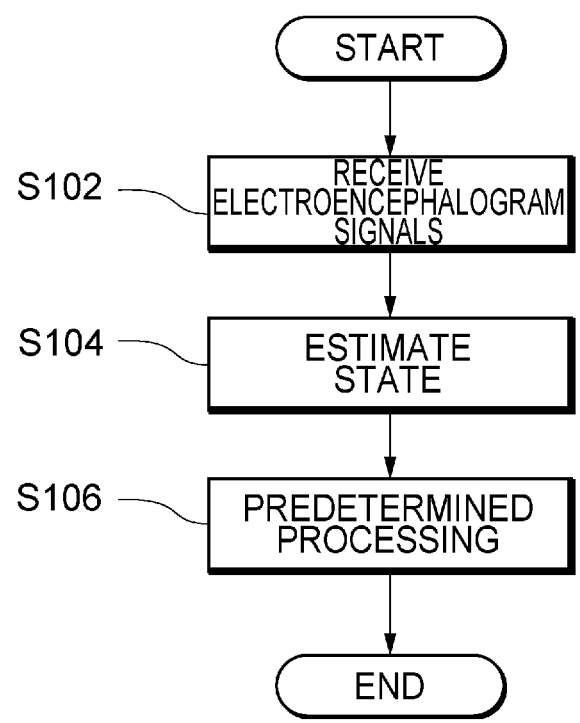
FIG. 12 is a flowchart showing an example of induction processing according to the second embodiment.

Next, operations of the electroencephalogram signal processing system 1 will be described. FIG. 12 is a flowchart showing an example of induction processing according to the second embodiment. In the example shown in FIG. 12, processing to induce to a predetermined state using acquired electroencephalogram signals is performed.

In step S102, the acquiring unit 212 acquires electroencephalogram signals output from sensors (e.g., the elastic electrodes of the earphones 10, etc.).

In step S104, the estimating unit 214 uses the model that has learned predetermined electroencephalogram signals of the wearer wearing the sensors and the state of the wearer at the time of acquiring these predetermined electroencephalogram signals to estimate the state of the wearer from the acquired electroencephalogram signals.

In step S106, the processing unit 216 executes predetermined processing on the basis of the estimated state of the wearer. The predetermined processing is processing of annunciation of the state to the wearer, or the like, for example.

Figure 13:
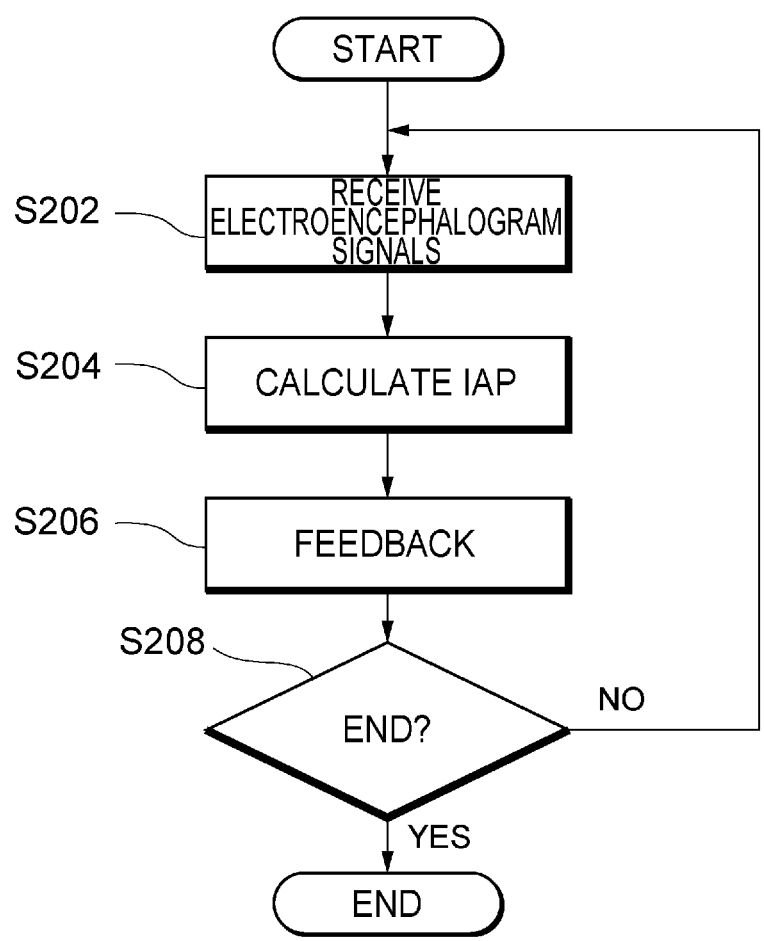
FIG. 13 is a flowchart showing an example of training processing according to the second embodiment.

FIG. 13 is a flowchart showing an example of training processing according to the second embodiment. The example shown in FIG. 13 shows processing of performing training so as to transition to a predetermined state, while sensing electroencephalogram signals.

In step S202, the acquiring unit 212 acquires electroencephalogram signals output from sensors (e.g., the elastic electrodes of the earphones 10, etc.).

In step S204, the processing unit 216 calculates an IAP (Individual Alpha frequency Peak) from the electroencephalogram signals.

In step S206, the processing unit 216 performs feedback regarding whether to move the IAP to high potential or to move to low potential, on the basis of the calculated IAP.

In step S208, the processing unit 216 determines whether or not the processing will end, on the basis of operations by the wearer. If the user performs an ending operation (Step S216—YES), the processing ends, and if the user does not perform an ending operation (Step S216—NO), the processing returns to step S202.

[Modifications]

Although a plurality of embodiments of the technology disclosed in the present application have been described above, the technology disclosed in the present application is not limited to the above. Also, programs of the information processing devices 20 and 30 according to the present invention can be installed or loaded to a computer through various types of non-transitory recording media such as optical disks like CD-ROMs and so forth, magnetic disks, semiconductor memory, and so forth, or by downloading over a communication network or the like.

Figure 14:
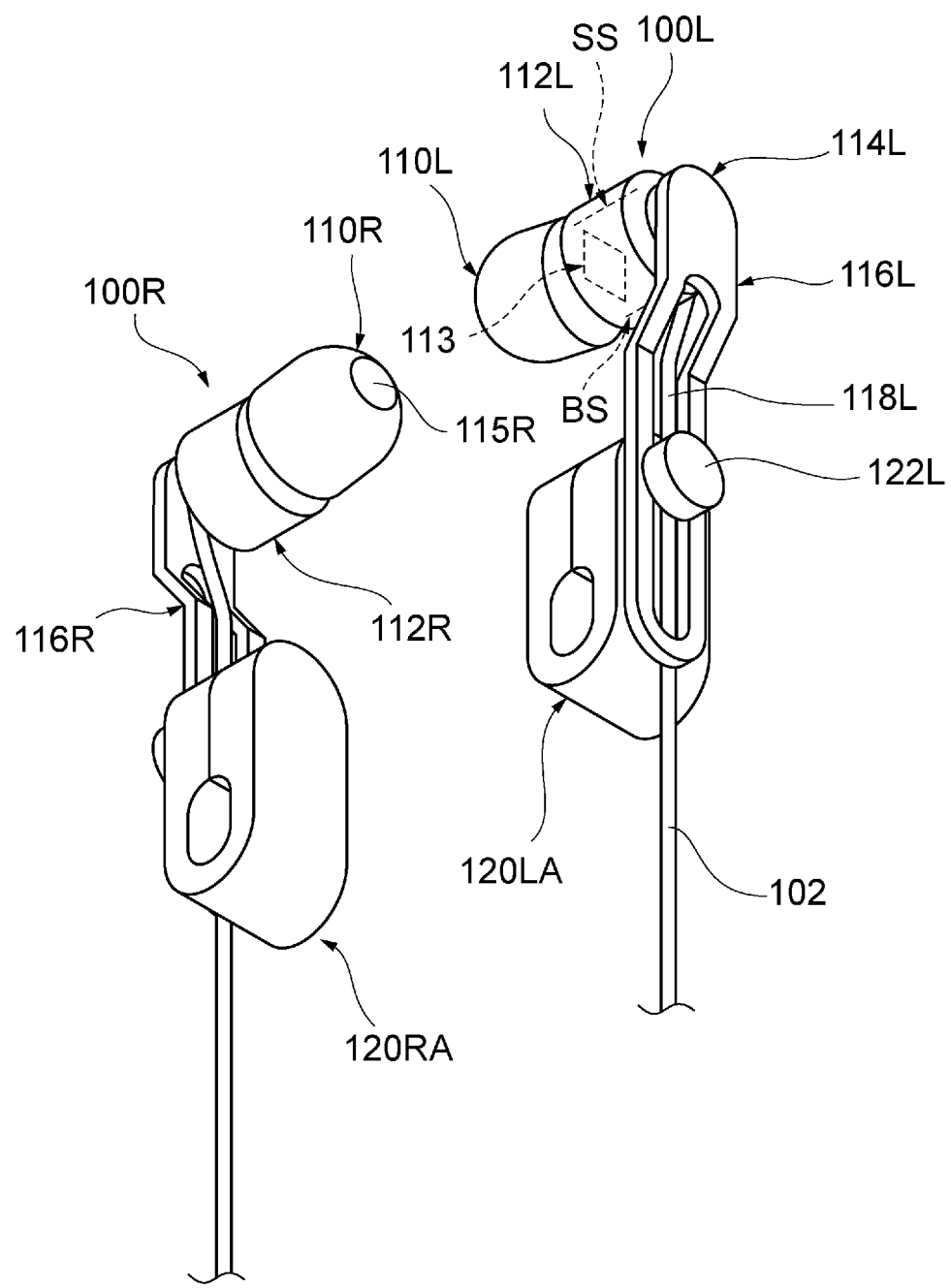
FIG. 14 is a diagram illustrating an enlarged example of earphones according to a Modification.

FIG. 14 is a diagram illustrating an enlarged example of earphones according to Modification 1. In the example of earphones illustrated in FIG. 14, the orientation of installation of the gripping portions 120 is different from that of the earphones illustrated in FIG. 2, and other configurations are the same as the earphones illustrated in FIG. 2. As illustrated in FIG. 14, gripping portions 120RA and 120LA are disposed with the longitudinal direction thereof following the Z direction in the vertical direction. Also, the longitudinal direction of the gripping portions 120 is provided following the direction of movement by the adjustment mechanisms provided to the connecting portions 116. The portions that pinch the earlobes face in an upward direction on a Z axis (in the direction of the housing). Accordingly, a greater part of the gripping portions 120 is hidden on the sides of the connecting portions 116 toward the face, and accordingly design can be improved. Also, by employing the configurations of the gripping portions 120 illustrated in FIG. 14, the size of the gripping portions 120 can be reduced. The reason is that, by gripping the earlobes from below as illustrated in FIG. 14, the longitudinal-direction length of the bent portions of the gripping portions 120 can be made to be shorter than when gripping the earlobes from the horizontal direction as illustrated in FIG. 1, since earlobes generally are wider in the horizontal direction.

Figure 15:
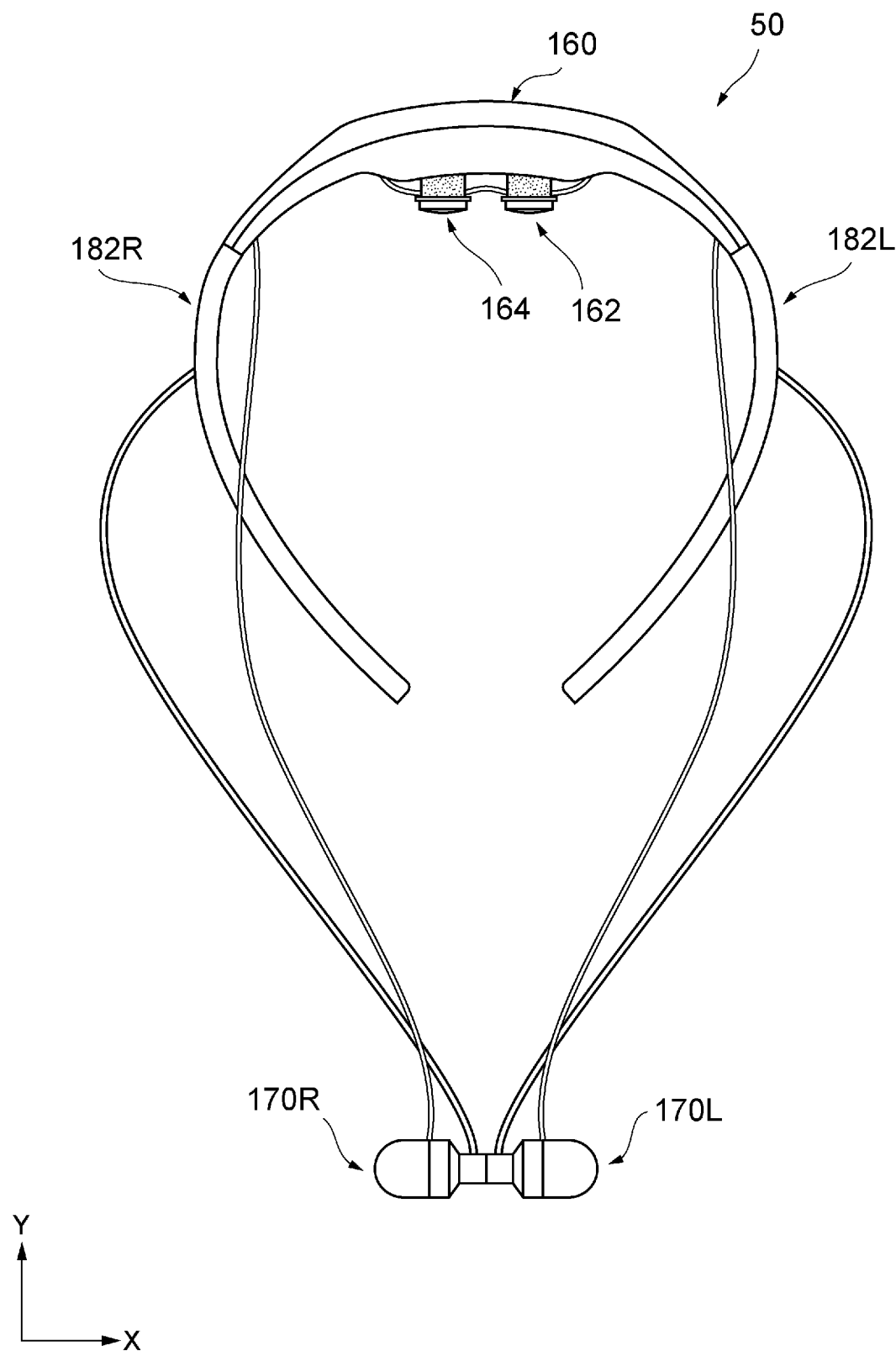
FIG. 15 is a diagram illustrating an example of an earphone set according to Modification 2.

FIG. 15 is a diagram illustrating an example of an earphone set 50 according to Modification 2. The earphone set 50 illustrated in FIG. 15 has no gripping portions 120 of the earphones illustrated in FIGS. 1 and 14, and instead has a neck-worn portion 160 and a pair of earphones 170R and 170L. The earphones 170R and 170L are connected to the neck-worn portion 160 by a cable capable of signal communication, but may be connected by wireless communication.

The neck-worn portion 160 has a middle member that follows the neck on the rearward side thereof, and rod-like members (arms) 182R and 182L having curved shapes that follow both sides of the neck. Electrodes 162 and 164 that sense electroencephalogram signals are provided on the surface of the middle member that comes into contact with the neck on the back side. The electrodes 162 and 164 are a grounding electrode and a reference electrode, respectively. Accordingly, the distance from the elastic electrodes provided to the eartips of the earphones can be increased, and electroencephalogram signals can be acquired with good precision. Also, distal end sides of the rod-like members 182R and 182L on both sides of the neck-worn portion 160 are heavier than the basal sides (on the side toward the middle member), and accordingly, the electrodes 162 and 164 are in appropriate pressure contact with the neck of the wearer. For example, weights are provided at the distal end sides of the rod-like members 182R and 182L.

Figure 16:
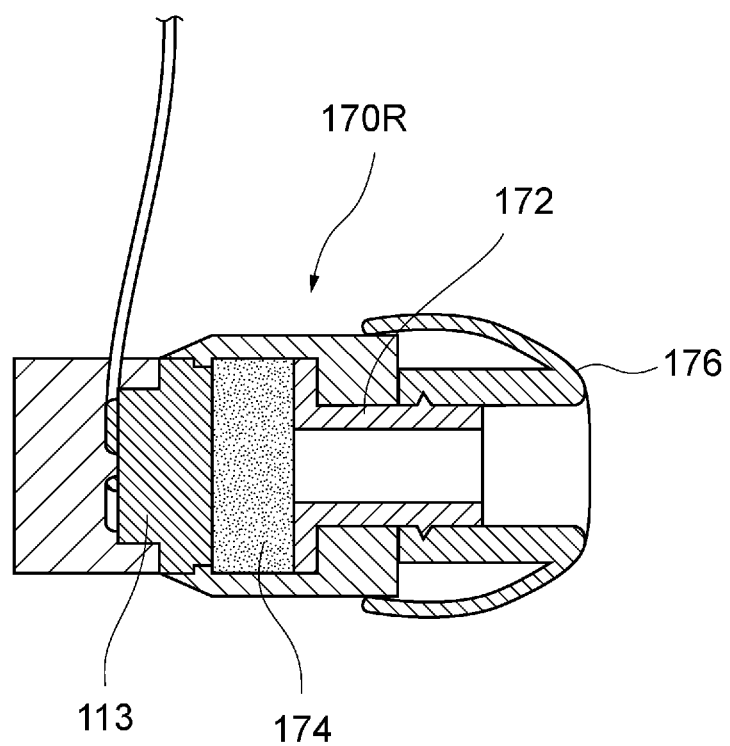
FIG. 16 is a diagram illustrating a schematic example of a cross-section of the earphone according to Modification 2.

FIG. 16 is a diagram illustrating a schematic example of a cross-section of the earphone 170 according to Modification 2. The earphone 170 illustrated in FIG. 16 is basically the same as the earphones 100, but an elastic member (e.g., urethane) 174 is provided between the speaker 113 and a nozzle 172. By providing this elastic member 174, vibrations of the speaker 113 are not readily conveyed to an elastic electrode of an eartip 176, and the elastic electrode of the eartip 176 and the speaker 113 can be prevented from interfering with respect to sound.

Further, the eartip 176 including the elastic electrode is situated at a sound conduit opening, and is capable of preventing interference due to sound vibrations by the elasticity of the elastic electrode itself. Also, by employing an elastic member for the housing, sound vibrations are not readily conveyed to the elastic electrode of the eartip 176 due to this elastic member, and interference due to sound vibrations can be prevented.

The earphones 170 include an audio sound processor, and sound signals no higher than a predetermined frequency equivalent to electroencephalogram signals (e.g., 50 Hz) are cut out using this audio sound processor. The audio sound processor particularly cuts out sound signals of 30 Hz and lower at which electroencephalogram signal characteristics tend to be manifested, but amplifies sound signals of frequencies around 70 Hz, to keep the base sound from being compromised. Accordingly, interference between sound signals and electroencephalogram signals can be prevented. The audio sound processor may also be arranged to cut out predetermined frequencies only in a case in which sensing of electroencephalogram signals is being performed. Note that the above-described audio sound processor is also applicable to the earphones 10 in the embodiments as well.

Figure 17:
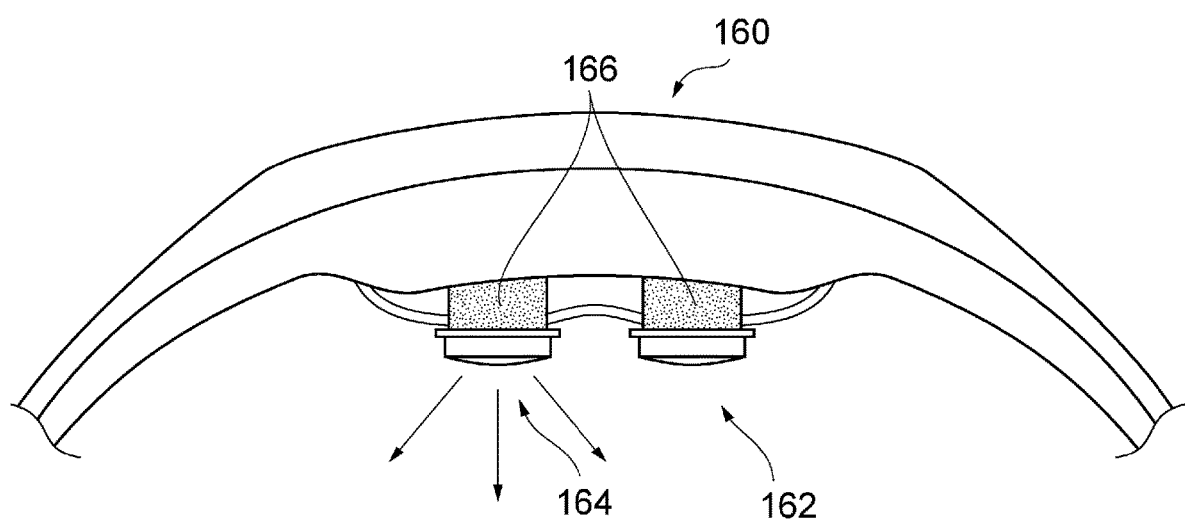
FIG. 17 is a diagram illustrating an example of a structure in a proximity of electrodes of a neck-worn portion according to Modification 2.

FIG. 17 is a diagram illustrating an example of the structure of the neck-worn portion 160 around the electrodes, according to Modification 2. In the example illustrated in FIG. 17, elastic members 166 are provided on the neck-worn portion 160 side of each of the electrodes 162 and 164. The elastic members 166 are made of urethane or the like for example, and the electrodes 162 and 164 are capable of positional change by the elasticity of the elastic members 166.

As a specific example, hemisphere-shaped electrodes are used, and the elastic members 166 are glued on covering the center portions of the hemispheres, thereby enabling the angle of the electrodes to be changed in 360 degrees using the elasticity of the elastic members 166. Also, the elastic members 166 are deformed in accordance with the shape of the neck of the wearer, and the electrodes 162 and 164 come into pressure contact with the neck of the wearer more readily.

As described above, the distal end sides of the rod-like members 182R and 182L on both sides of the neck-worn portion 160 are heavy, and accordingly when the neck-worn portion 160 is draped over the neck, the electrodes 162 and 164 come into pressure contact with the neck of the wearer more readily due to the weighting of the distal end sides of the rod-like members 182R and 182L.

Figure 18:
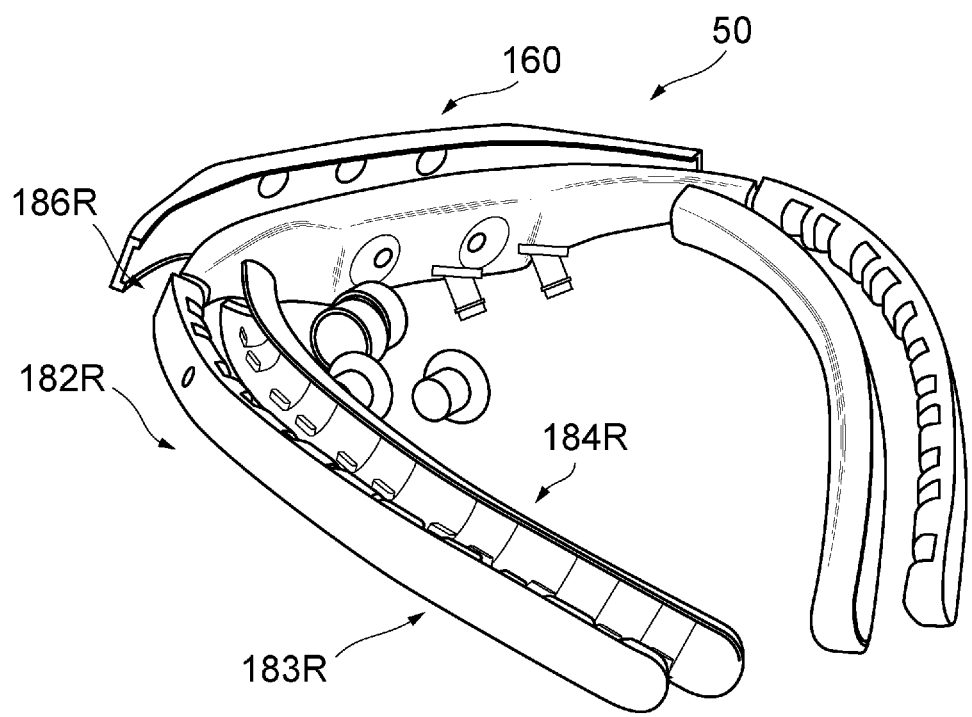
FIG. 18 is a diagram illustrating an example of a schematic disassembled view of the earphone set according to Modification 2.

FIG. 18 is a diagram illustrating an example of a schematic disassembled view of the earphone set 50 according to Modification 2. In the example illustrated in FIG. 18, the rod-like member 182R has an accordion structure on the inner side of an aluminum plate situated on the outer side for example, and the rod-like member 182R is deformable in accordance with the shape, thickness, and so forth, of the neck of the wearer. Also, an elastic member 184R of rubber or the like is provided on the inner side of the rod-like member 182R toward the neck, and the burden of contact to the neck can be mitigated and comfort of wear improved, by the elastic member 184R coming into contact with the neck.

Also, the rod-like members 182 on both sides of the neck-worn portion 160 can each be folded away to the electrode side. For example, the rod-like member 182R can be folded away to the electrode side or the middle member side by a foldaway structure 186R. Note that the rod-like member 182L also has a foldaway structure (e.g., a hinge) in the same way, and can be folded away to the electrode side. Accordingly, the neck-worn portion 160 can be compactly stored.

Also, the rod-like members 182R and 182L are shaped slightly curved downward in the vertical direction, so that the rod-like members 182R and 182L readily follow the collarbones of the wearer.

Specific Example of Electroencephalogram Feedback Training

Next, a specific example of the above-described electroencephalogram feedback training for each individual will be described. This specific example is an application that manages concentration time and break time while learning electroencephalogram signals, and is capable of improving productivity. This application segments time, for example, and performs training while changing usage cases according to each time section. For example, meditation is performed for the first ten minutes (usage case of meditation), a task is performed for the next 25 minutes (usage case of concentration), and a break is taken for the next five minutes (usage case of relaxation), and four sets of the task and break are performed. Note that the final break may be 25 minutes. This time management technique draws on the time management technique of the Pomodoro Technique, which is said to improve productivity.

During the time management of the specific example, the acquiring unit 212 acquires electroencephalogram signals using the earphones and so forth described above, the estimating unit 214 estimates the current state of the electroencephalogram signals of the user in each usage case, using the trained model that has been individually customized by the learning unit 311, and the processing unit 216 performs induction processing to transition from the current state to a good state for this user.

As one example of feedback, the processing unit 216 controls a gradation display using colors allocated in advance to the frequency bands of the electroencephalogram signals in a predetermined region of the display screen of the user terminal 20, such as in the background, for example. When the electroencephalogram signals are transitioning to a good state (state of golden ratio), the color of the predetermined region is displayed gradually changing to a bright color, and when the electroencephalogram signals are not transitioning to a good state, the color of the processing region is displayed gradually changing to a dark color, for example. Note that the good state of electroencephalogram signals differs depending on the user, and accordingly the gradation is decided with reference to the frequency bands of the electroencephalogram signals of that user in a good state. Accordingly, the gradation can be display in the predetermined region in accordance with change of the electroencephalogram signals, and the current state of the electroencephalogram signals can be visually expressed to the user.

Figure 19A:
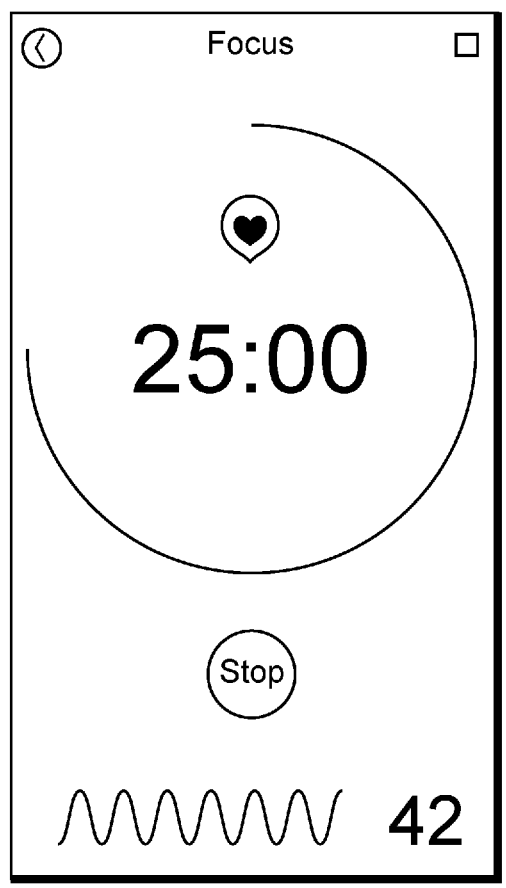
FIG. 19A is a diagram illustrating an example of a display screen during training for concentration.

FIG. 19A is a diagram illustrating an example of a display screen during concentration training. The screen illustrated in FIG. 19A is a screen displayed during the task in time management, indicating that the current score value is "42", and "25:00" indicates a timer for the task time. In this way, the processing unit 216 uses a timer for time management of each usage case. The processing unit 216 may also display waveforms of the frequency bands of the electroencephalogram signals relating to each usage case.

Also, the processing unit 216 may perform control to output a sound that is set in advance for the frequency bands of the electroencephalogram signals from a speaker. The sounds set in advance are natural sounds, for example, such as sounds of wind, rain, waves, forests, and so forth, and may be sounds of these combined as appropriate. For example, when the electroencephalogram signals are transitioning to a good state (state of golden ratio), sound that gradually becomes gentler is output from the speaker, and when the electroencephalogram signals are not transitioning to a good state, sound that gradually becomes more agitated is output from the speaker. The phrase, the electroencephalogram signals are transitioning to a good state, means that the difference between the ratio of the average values or representative values in the frequency bands of the current electroencephalogram signals as to the golden ratio is becoming smaller, and the frequency bands are the same as the frequency bands regarding which the golden ratio is obtained. Also, the sound set in advance may be voice. Note that in a case in which the electroencephalogram signals acquired by the acquiring unit 212 are drawing near to the above-described golden ratio, the processing unit 216 may display emoji on the screen, output sound, display a color on the screen, and so forth.

Note that the application in the specific example can create scores for and visualize concentration, relaxation, tension, fatigue, and so forth, determined from the electroencephalogram signals, for predetermined periods, such as for example, in increments of months, in increments of weeks, in increments of days, or in increments of sessions. As for the score, the estimating unit 214 creates scores on the basis of distance between the golden ratio learned using electroencephalogram signals of individual users, and the ratio of the representative value of each of the frequency bands obtained by dividing the current electroencephalogram signals into the frequency bands, for each of the usage cases, and the processing unit 216 displays the score values of the created score on the screen.

Figure 19B:
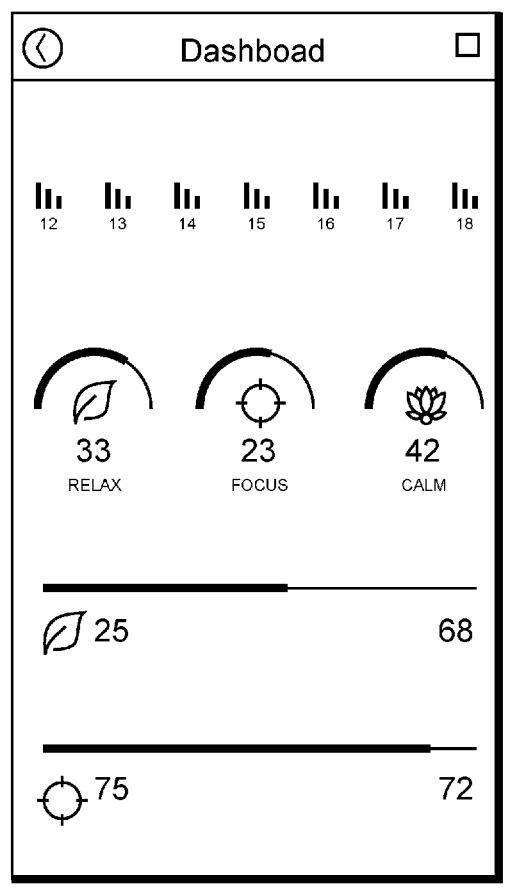
FIG. 19B is a diagram illustrating an example of a screen that displays measurement results relating to relaxation, concentration, and meditation, in one-day increments.

FIG. 19B is a diagram illustrating an example of a screen displaying measurement results relating to relaxation (Relax), concentration (Focus), and meditation (CALM) in one-day increments. The screen illustrated in FIG. 19B is a so-called dashboard that tallies and visualizes data, and indicates that, on the basis of the electroencephalogram signals measured on the 15th (Wed), the amount of time that the user has been determined to be able to relax is "33 minutes", the amount of time that the user has been determined to be able to concentrate is "23 minutes", and the amount of time that the user has been determined to be calm (to be able to meditate) is "42 minutes".

The estimating unit 214 may obtain the score value for each estimation processing performed using the trained model, in each of the usage cases. In the example illustrated in FIG. 19B, the score value for relaxation indicates "68", and the score value for concentration indicates "72". Note that in a case in which the score value of each of the usage cases is no less than a corresponding predetermined value, the processing unit 216 may determine that the user is able to relax, is able to concentrate, or is calm. Each usage case regarding which time management is performed will be described below.

(Meditation)

Meditation (calmness) is performed in the first time section, for example, in the time management technique of the present application. First, the processing unit 216 performs meditation guidance, using audio and video. The acquiring unit 212 acquires electroencephalogram signals following the meditation guidance, the estimating unit 214 calculates a score value on the basis of the acquired electroencephalogram signals and the golden ratio, and upon the electroencephalogram signals calming and the score value rising (the frequency drawing near to the golden ratio), the processing unit 216 changes the background color, and performs control such that wind in the background image is stilled and/or birds sing, or the like.

Conversely, when the electroencephalogram signals are disturbed, and the score value falls (the frequency is distanced from the golden ratio), the processing unit 216 performs control such that the color of the background is changed, wind blows in the background image and/or the scenery of the background image becomes stormy. The processing unit 216 may also change background (natural environment) and contents of guidance in accordance with the time of day (morning, afternoon, etc.) at which the application is being executed or the object thereof.

Figure 20:
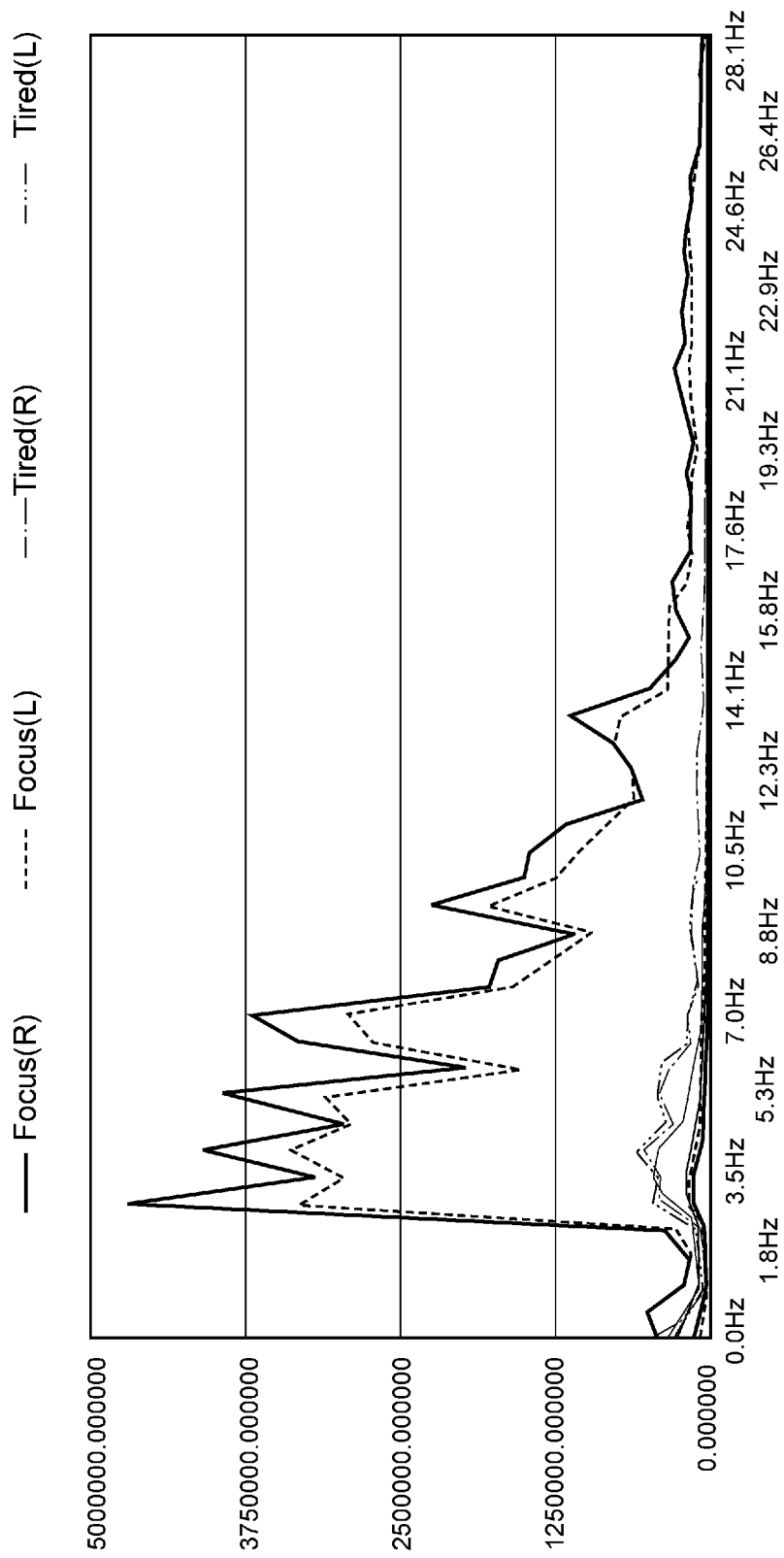
FIG. 20 is a diagram showing an example of frequency waveforms when meditating and when other than meditating.

FIG. 20 is a diagram showing an example of frequency waveforms when meditating and when other than meditating. In the example shown in FIG. 20, low-frequency waves of delta waves and theta waves appear when meditating (Focus) as compared to when other than meditating (Tired). Characteristics of these individual waveforms are used to find the golden ratio and so forth of the user individual. Also, audio and video such as described above are used to perform meditation guidance, in order to cause delta waves and theta waves to appear from the current frequency value.

(Task)

A task (concentration, fatigue) is performed following meditation in the time management technique of the present application, and thereafter is performed alternatingly with breaks. The estimating unit 214 estimates the concentration and degree of fatigue of the user on the basis of the frequency of the acquired electroencephalogram signals. For example, when there is an increase in theta waves during the task, the estimating unit 214 estimates that fatigue is increasing. This is because it is said that delta waves and theta waves generally do not appear in an awakened state.

Figure 21:
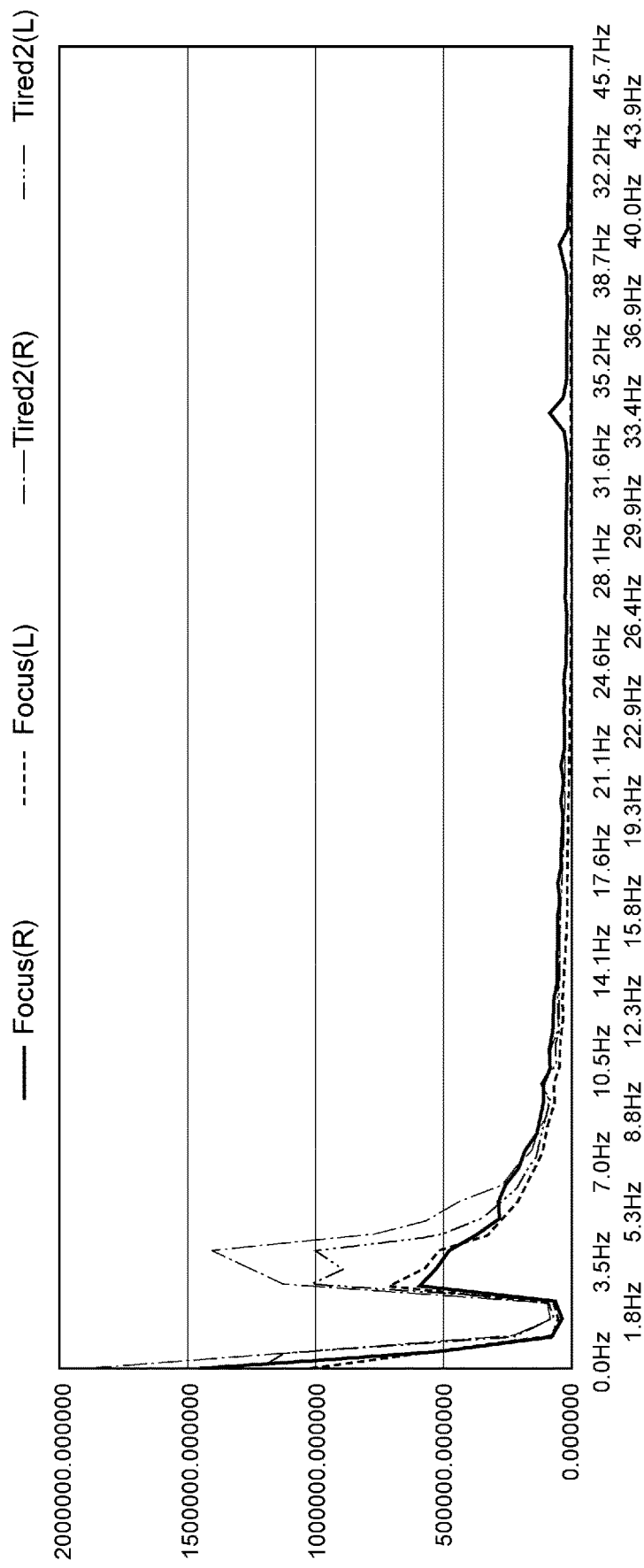
FIG. 21 is a diagram showing an example of frequency waveforms of electroencephalogram signals in the morning and after lunch.

FIG. 21 is a diagram showing an example of frequency waveforms of electroencephalogram signals in the morning and after lunch. In the example shown in FIG. 21, the value of theta waves is not great during the morning (Focus), but the value of theta waves increases after lunch (Tired2) when the user is feeling fatigue or drowsiness. When the value of theta waves increases, the processing unit 216 plays a sound or the like to prompt the user to concentrate, in order to lower the value of theta waves. Note that in a concentrated state, the amplitude of the frequency bands is constant with little variance, and the golden ratio appropriately appears.

(Break)

Breaks (breaks, concentration) are taken following tasks in the time management technique of the present application, and thereafter are performed alternatingly with tasks. It is said that alpha waves appear when the eyes are closed, and accordingly the estimating unit 214 can estimate that the eyes are closed when the value of alpha waves becomes great. Also, when a meditating state is entered, the low-frequency values of delta waves and theta waves rise, and accordingly when the values of these frequency bands become great, the estimating unit 214 estimates that the user is calming down. Also, if the user is awake during a break, the processing unit 216 provides contents presented by the trained model that will cause this user to calm down.

Note that the frequency of the electroencephalogram signals in each usage case is obtained by subjecting frequency signals, obtained by time-segmenting and conversion of electroencephalogram signals, to signal averaging of frequency signals within a predetermined time. The predetermined time may also be different for each usage case.

Accordingly, the application of the specific example can support the optimal way of using time by using each time band time-segmented for each usage case. Also, this application can create a playlist that enables concentration, in accordance with personal preferences and characteristics, within the concentration time in time management. For example, using the trained model that has learned the results of annotation by the user enables selecting tunes for transitioning to a good state (state of golden ratio), and a playlist is generated in which these tunes are imparted an order according to a predetermined reference. Also, during breaks in the time management, this application can recommend guidance such as simple meditation or stretching exercises, games or videos, or the like, to pacify the brain, in accordance with characteristics of the electroencephalogram signals of the user, using the trained model.

<Analysis of Heartbeat or Respiration>

Figure 22:
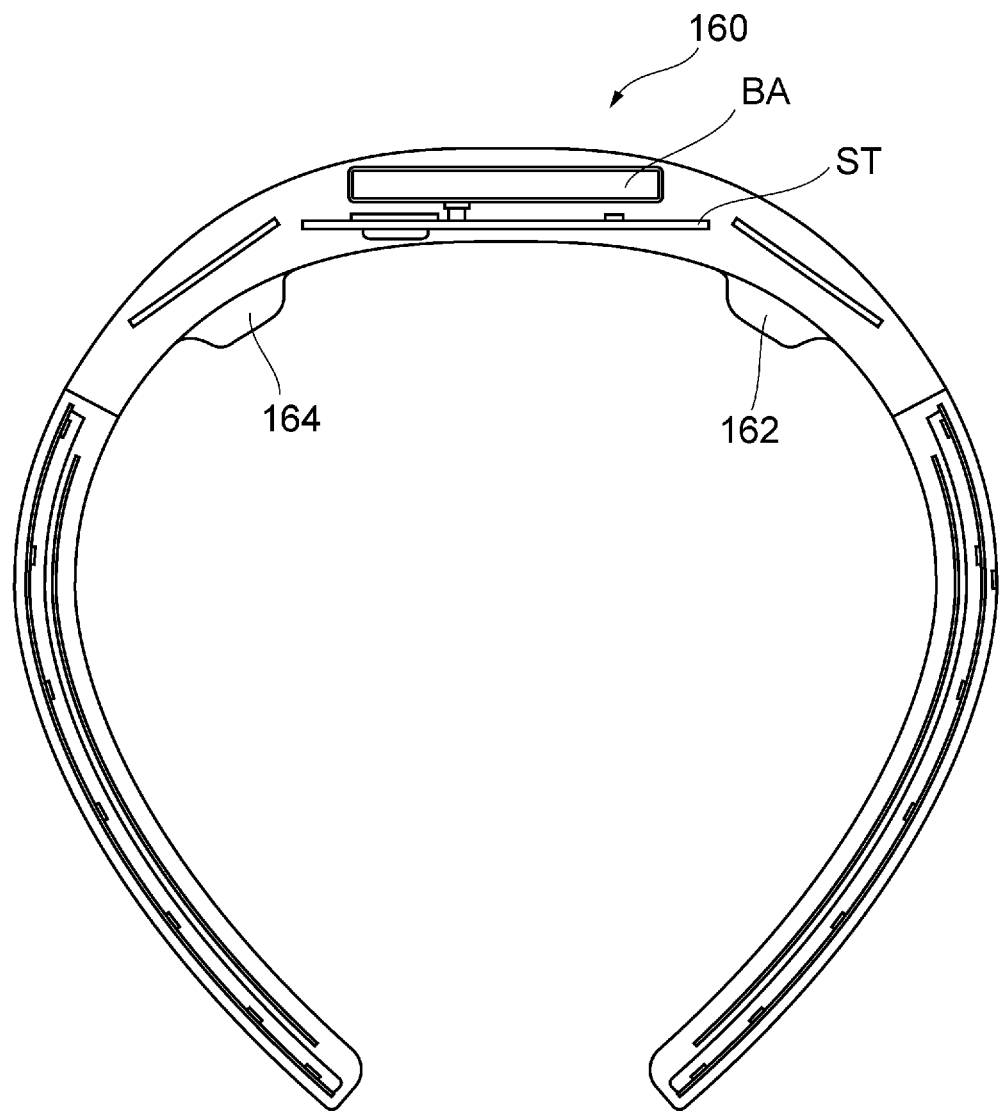
FIG. 22 is a diagram illustrating an example of positions of electrodes of a neck-worn portion according to Modification 3.

In Modification 3, electrocardiogram signals (ECG: Electrocardiogram) are measured on the basis of the pulse at the carotid artery, by changing the positions of the reference electrodes of the neck-worn portion 160 in Modification 2. FIG. 22 is a diagram illustrating an example of each part of the neck-worn portion 160 according to Modification 3. The example illustrated in FIG. 22 represents a cross-sectional view of the neck-worn portion 160 along the XY plane with the electrodes 162 and 164 being disposed so as to be positioned on both sides of the neck of the wearer, and are configured of elastic electrodes. For example, the electrodes may be disposed on the rod-like members situated on both sides of the neck or on both end portions of the middle member out of the parts of the neck-worn portion 160, or the electrodes 162 and 164 may be disposed at positions a predetermined distance (e.g., 3 to 7 cm) away from the middle of the neck-worn portion 160 to the right and left. Also, a battery BA and a circuit board ST on which a processing unit is mounted are provided at a middle portion inside of the neck-worn portion 160. Disposing the circuit board ST on the side closer to the neck, and disposing the battery BA that is shorter in the X direction than the circuit board ST on the outer side from the circuit board ST enables the neck-worn portion 160 to have a curved shape that follows the neck better. Also, an arrangement may be made in which an attachable elastic member is provided on the inward side of the neck-worn portion 160, with the electrodes 162 and 164 provided to this elastic member. Accordingly, the elastic member is in close contact with the neck of the wearer even in cases with movement, such as when exercising, and accordingly reference signals can be acquired with good precision.

Figure 23:
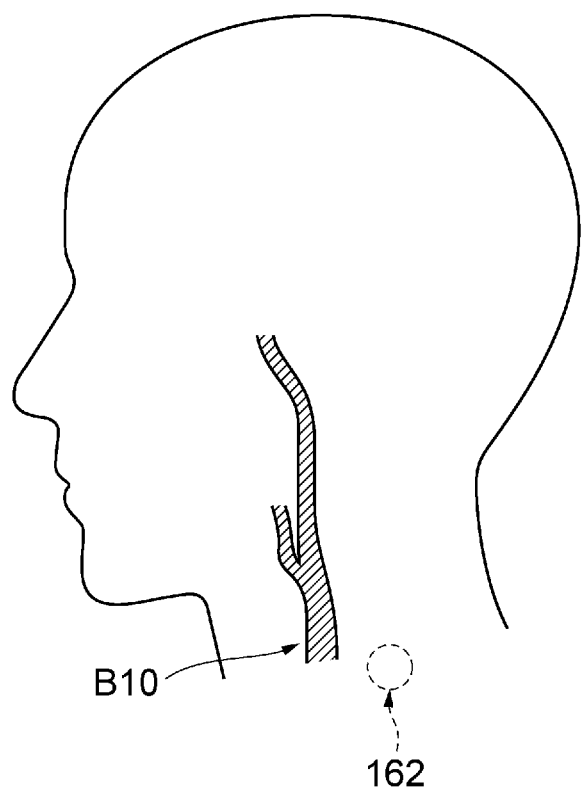
FIG. 23 is a diagram illustrating a positional relation between a carotid artery and a left electrode 162.

FIG. 23 is a diagram illustrating a positional relation between the carotid artery and the left electrode 162. In the example illustrated in FIG. 23, signals based on the pulse of the carotid artery are included in the signals sensed by the electrode 162 by positioning the electrode 162 in the vicinity of the carotid artery B10.

Figure 24:
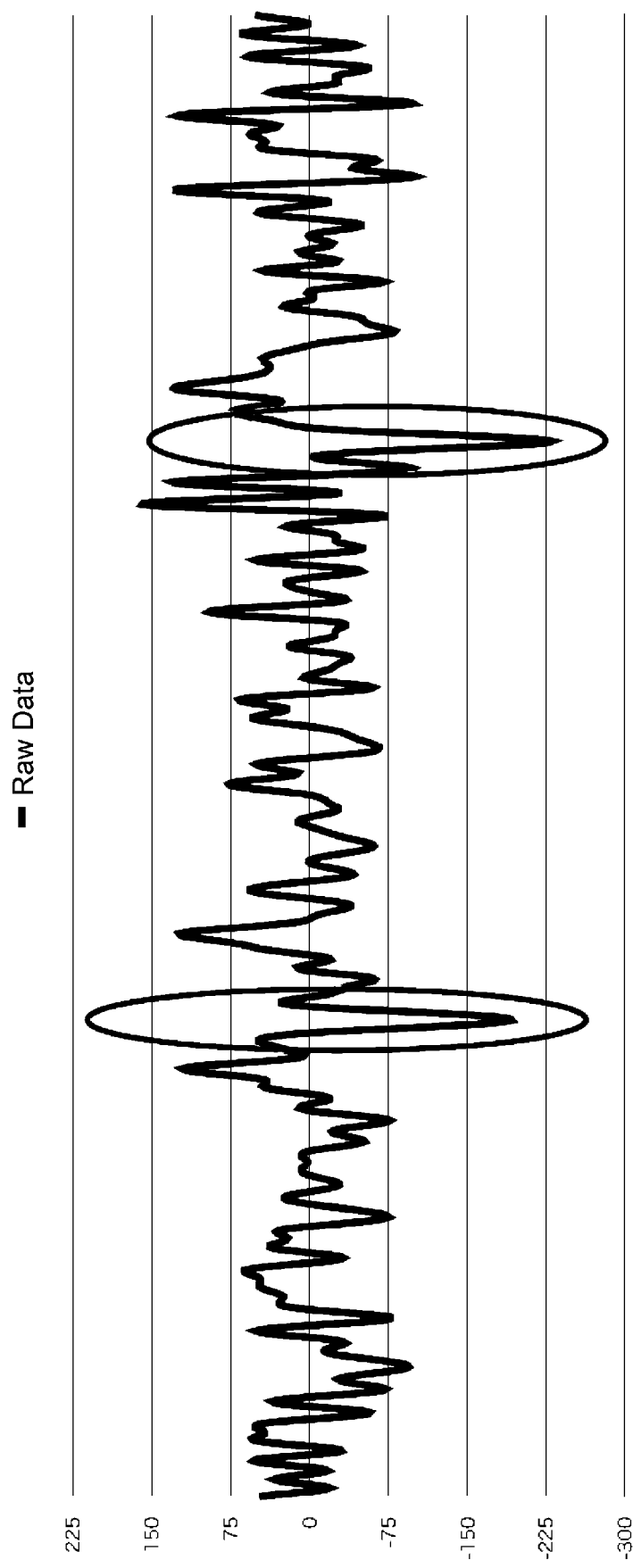
FIG. 24 is a diagram showing an example of reference signals in which pulses of the carotid artery have become intermingled.

FIG. 24 is a diagram showing an example of reference signals in which pulses of the carotid artery have become intermingled. The example shown in FIG. 24 is an example of raw data of data sensed by the electrodes 162 or 164. In the graph shown in FIG. 24, the vertical axis represents the value of sensed signals, and the horizontal axis represents time. The reference signal is a signal subtracted from the signals sensed by the elastic electrodes of the eartips 176, and accordingly the electrocardiogram signals (ECG) intermingled in the reference signals are measured in inverse phase, as shown in FIG. 24. For example, the peaks protruding downward that are encircled in FIG. 24 are signals indicating the electrocardiogram signals. Signals indicating a normal pulse of the wearer are synonymous with electrocardiogram signals.

Using the intermingling of the pulse of the carotid artery, the CPU 210 acquires electroencephalogram signals based on signals output from the elastic electrodes of the eartips 176, with the signals output from the electrodes 162 and 164 provided to the neck-worn portion described in Modification 3 as reference signals, for example. Next, the CPU 210 detects the pulse on the basis of the peak appearing in inverse phase from the peak of the acquired electroencephalogram signals.

Accordingly, disposing the positions of the electrodes measuring reference signals so as to be situated at both sides of the neck of the wearer enables electroencephalogram signals and electrocardiogram signals to be measured using common signals. That is to say, the CPU 210 can analyze electroencephalogram signals, and also analyze the heartbeat by measuring the electrocardiogram signals based on the pulse.

Next, an example of measuring respiration using the neck-worn portion 160 according to Modification 3 will be described. The electroencephalogram signals are subjected to predetermined filter processing in order to measure respiration. The predetermined filter processing is preformed according to the following procedures.

1: Low-pass filter
2: Median filter
3: Subsequently, calculate value of power spectrum by FFT (fast Fourier transform)
4: Calculate energy difference value indicating time derivative ($P_t - P_{t-1}$) from time-series power spectrum ($P_t$ is power spectrum value at time t)

Figure 25A:
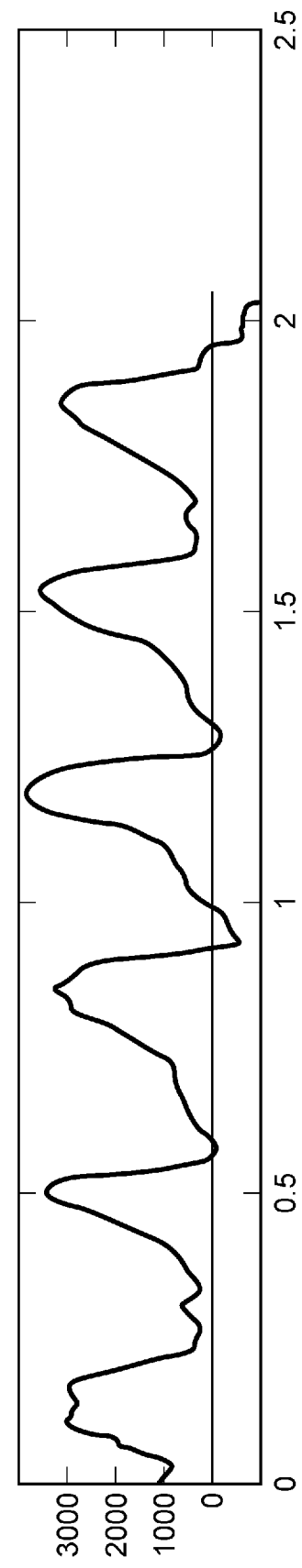
FIG. 25A is a diagram showing an example of signals when breathing through the mouth.
Figure 25B:
FIG. 25B is a diagram showing an example of signals when breathing through the nose.

FIG. 25A is a diagram showing an example of signals when breathing through the mouth. FIG. 25B is a diagram showing an example of signals when breathing through the nose. In the graphs in FIGS. 25A and 25B, the vertical axis represents the energy difference value following filter processing, and the horizontal axis represents time. In the signals in FIGS. 25A and 25B, the portions protruding downward appear when breathing in (inhaling), and the portions protruding upward appear when breathing out (exhaling). One factor why such peaks and valleys appear is thought to be that change in the facial muscle potential when breathing feeds over into the electrodes of the eartips 176.

Using the above-described change in muscle potential, the CPU 210 acquires electroencephalogram signals based on signals output from the elastic electrodes of the eartips 176, with the signals output from the electrodes 162 and 164 provided to the neck-worn portion described in Modification 3 as reference signals, for example. Next, the CPU 210 performs low-pass filter and median filter processing on the acquired electroencephalogram signals, performs frequency transform of the signals following filter processing, performs time derivation of the time-series power spectrum value following frequency transform, and detects respiration on the basis of cyclicity of the time-derivative difference values.

Accordingly, performing predetermined filter processing on the electroencephalogram signals enables signals representing respiration to be measured. That is to say, the CPU 210 can, while analyzing electroencephalogram signals, also measure signals representing respiration and analyze respiratory rate, depth, and so forth.

Also, applying the predetermined filter processing used for respiratory detection to heartbeat detection as well enables noise to be removed, and the heartbeat to be detected more appropriately. That is to say, the CPU 210 executes detecting the electrocardiogram peaks appearing in inverse phase from the peaks of the electroencephalogram signals, subjecting the detected signals to low-pass filter and median filter processing, performing frequency transform of the signals following filter processing, performing time derivation of the time-series power spectrum value following frequency transform, and detecting the pulse on the basis of cyclicity of the time-derivative difference values. Accordingly, the heartbeat can be detected using the pulse from which noise is removed.

Note that in the analysis of heartbeat and respiration described above, the CPU 210 finds cyclicity from data values shown in FIG. 24 or 25 using an autocorrelation function, thereby detecting the heartbeat and respiration. Also, the above-described processing for detecting the heartbeat and respiration may be executed by being implemented as a program including commands for each process, which is installed in an information processing device.

REFERENCE SIGNS LIST

10 Earphones
20, 30 Information processing device
110 Eartip (elastic electrode)
112 Housing
113 Speaker
114 Joint mechanism
116 Connecting portion
118 Cable
120 Gripping portion
212 Acquiring unit
214 Estimating unit
216 Processing unit
311 Learning unit

What is claimed is:

1. An information processing device, comprising:
an acquiring unit that acquires an electroencephalogram signal output from an earphone comprising a housing, a speaker accommodated inside the housing and an eartip that is mounted on an end portion side of the housing, and that includes a sound conduit portion through which sound from the speaker passes, and an elastic electrode that performs sensing of an electroencephalogram of a wearer;
an estimating unit that estimates a state of a wearer from the acquired electroencephalogram signal, using a model that has learned a predetermined electroencephalogram signal of the wearer of the earphone and a state of the wearer at the time of acquiring the predetermined electroencephalogram signal; and
a processing unit that performs processing on the basis of the state of the wearer that is estimated, wherein the model is a customized model in which a predetermined model, which is trained regarding an electroencephalogram signal of another person and a state of the another person at the time of acquiring the electroencephalogram signal of the another person, has additionally learned the electroencephalogram signal of the wearer and the state of the wearer at the time of acquiring the electroencephalogram signal of the wearer.

2. An information processing device, comprising:
an acquiring unit that acquires an electroencephalogram signal output from an earphone comprising a housing, a speaker accommodated inside the housing, an eartip that is mounted on an end portion side of the housing, and that includes a sound conduit portion through which sound from the speaker passes, and an elastic electrode that performs sensing of an electroencephalogram of a wearer;
an estimating unit that estimates a state of a wearer from the acquired electroencephalogram signal, using a model that has learned a predetermined electroencephalogram signal of the wearer of the earphone and a state of the wearer at the time of acquiring the predetermined electroencephalogram signal; and
a processing unit that performs processing on the basis of the state of the wearer that is estimated, wherein the processing unit performs induction processing for inducing transition from the state of the wearer estimated on the basis of a current electroencephalogram signal to a predetermined state of the wearer indicated by a first electroencephalogram signal, wherein feedback to the wearer is performed on the basis of the current electroencephalogram signal.

3. An information processing method, comprising one or a plurality of processors included in an information processing device executing:
acquiring an electroencephalogram signal output from an earphone comprising, a housing, a speaker accommodated inside the housing, an eartip that is mounted on the end portion side of the housing, and that includes a sound conduit portion through which sound from the speaker passes, and an elastic electrode that performs sensing of an electroencephalogram of a wearer;
estimating a state of the wearer from the acquired electroencephalogram signal, using a model that has learned a predetermined electroencephalogram signal of the wearer of the earphone and a state of the wearer at the time of acquiring the predetermined electroencephalogram signal; and
performing processing on the basis of the state of the wearer that is estimated,
wherein the model is a customized model in which a predetermined model, which is trained regarding an electroencephalogram signal of another person and a state of the another person at the time of acquiring this electroencephalogram signal, has additionally learned the electroencephalogram signal of the wearer and the state of the wearer at the time of acquiring the electroencephalogram signal.

4. An information processing method, comprising one or a plurality of processors included in an information processing device executing, acquiring an electroencephalogram signal output from an earphone comprising a housing, a speaker accommodated inside the housing, an eartip that is mounted on an end portion side of the housing, and that includes a sound conduit portion through which sound from the speaker passes, and an elastic electrode that performs sensing of an electroencephalogram of a wearer;

estimating a state of the wearer from the acquired electroencephalogram signal, using a model that has learned a predetermined electroencephalogram signal of the wearer of the earphone and a state of the wearer at the time of acquiring the predetermined electroencephalogram signal; and performing processing on the basis of the state of the wearer that is estimated, wherein the performing comprises performing induction processing of inducing transition from the state of the wearer estimated on the basis of the current electroencephalogram signal to a predetermined state of the wearer indicated by a first electroencephalogram signal, in which induction processing, feedback to the wearer is performed on the basis of the current electroencephalogram signal.

\* \* \* \* \*